United States Patent
Schulze zur Wiesche et al.

(10) Patent No.: US 8,894,984 B2
(45) Date of Patent: *Nov. 25, 2014

(54) HAIR TREATMENT AGENT COMPRISING 4-MORPHOLINO-METHYL-SUBSTITUTED SILICONE(S)

(71) Applicant: Henkel AG & Co. KGaA, Duesseldorf (DE)

(72) Inventors: Erik Schulze zur Wiesche, Hamburg (DE); Markus Semrau, Langenfeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/287,278

(22) Filed: May 27, 2014

(65) Prior Publication Data

US 2014/0261516 A1  Sep. 18, 2014

Related U.S. Application Data

(63) Continuation of application No. PCT/EP2012/070918, filed on Oct. 23, 2012.

(30) Foreign Application Priority Data

Nov. 29, 2011 (DE) .......................... 10 2011 087 343

(51) Int. Cl.
*A61Q 5/00* (2006.01)
*A61Q 5/12* (2006.01)
*A61Q 5/06* (2006.01)
*A61K 8/898* (2006.01)
*A61Q 5/02* (2006.01)
*A61Q 5/04* (2006.01)

(52) U.S. Cl.
CPC . *A61K 8/898* (2013.01); *A61Q 5/12* (2013.01); *A61Q 5/06* (2013.01); *A61Q 5/02* (2013.01); *A61Q 5/04* (2013.01)
USPC ...................................... 424/70.122; 424/489

(58) Field of Classification Search
CPC ......... A61K 8/25; A61K 8/585; A61K 8/898; A61Q 5/04; A61Q 5/06; A61Q 5/12
USPC ............................................. 424/70.122, 489
See application file for complete search history.

(56) References Cited

U.S. PATENT DOCUMENTS 6,824,764 B2 * 11/2004 Devin-Baudoin et al. ... 424/70.1

OTHER PUBLICATIONS

STIC Search Report dated Jun. 17, 2014.*

* cited by examiner

*Primary Examiner* — Eisa Elhilo
(74) *Attorney, Agent, or Firm* — David K. Benson

(57) ABSTRACT

Hair treatment agents include at least one 4-morpholino-methyl-substituted silicone, which comprises in each case at least one of the structural units of the formulae (I), (II) and (III) as described herein, where * is a bond to one of the structural units (I), (II) or (III) or an end group B (Si-bound) or D (O-bound); B represents a group —OH, —O—Si(CH$_3$)$_3$, —O—Si(CH$_3$)$_2$OH, —O—Si(CH$_3$)$_2$OCH$_3$; D represents a group —H; —Si(CH$_3$)$_3$, —Si(CH$_3$)$_2$OH, —Si(CH$_3$)$_2$OCH$_3$; A represents an O-bound structural unit (I), (II) or (III) or an O-bound oligomeric or polymeric radical including structural units of the formulae (I), (II) or (III) or half of a connecting O atom to a structural unit (III) or represents —OH; n, m and o represent whole numbers between 1 and 1000.

9 Claims, No Drawings

HAIR TREATMENT AGENT COMPRISING 4-MORPHOLINO-METHYL-SUBSTITUTED SILICONE(S)

FIELD OF THE INVENTION

The present invention generally relates to hair treatment agents including specially substituted silicone(s) and to the use of these agents for the cleaning and/or care of hair.

BACKGROUND OF THE INVENTION

Care agents for keratinic fibers affect the natural structure and the properties of hair. Thus, following such treatments, for example the wet and dry combability of hair, the hold and the body of hair can be optimized or the hair can be protected against an increase in split ends. For a long time, it has therefore been common to subject the hair to a special after-treatment. This involves a hair treatment, generally in the form of a rinse, with special active substances, for example quaternary ammonium salts or special polymers. As a result of this treatment—depending on the formulation—the combability, hold and body of the hair are improved and the rate of split end formation is reduced.

In addition, so-called combination preparations have recently been developed with a view to reducing the effort involved in conventional multistage processes. In addition to the conventional components, for example for cleaning the hair, these preparations also include active substances which were previously reserved for hair after-treatment agents. Accordingly, the consumer saves one application step. At the same time, packaging costs are reduced because one product less is used. However, the known active substances cannot adequately meet all requirements. A need therefore still exists for active substances or active substance combinations for cosmetic agents with good care properties and good biodegradability. In surfactant- and/or electrolyte-including formulations in particular, there is a need for additional active care substances that can be incorporated into known formulations without any problems and which are not weakened in their action there as a result of incompatibilities with other ingredients.

Silicones, and among these amino functional silicones, are known as care substances in hair treatment agents, and corresponding products are widely available on the market. However, the need still exists to improve the effects achieved, particularly in respect of the handle, combability, softness and volume of the hair or hairstyle, and to reduce the quantities used.

It is therefore desirable to provide silicone-including hair treatment agents which impart even better properties to the hair treated therewith than hair treatment agents with known amodimethicones. In addition, even when significantly reduced quantities are used, it should be possible to achieve equally good or better effects. In particular, the products should improve the handle, combability, softness and volume of the hair or hairstyle and significantly minimize the contact angle of drops of water contacting the treated hair, which is a measure of the product performance.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A hair treatment agent including at least one 4-morpholinomethyl-substituted silicone, which in each case comprises at least one of the structural units of formulae (I), (II) and (III)

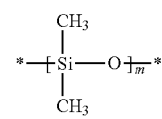

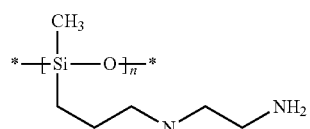

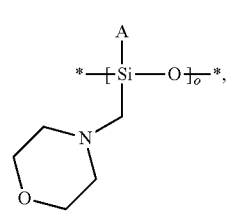

where * denotes a bond to one of the structural units (I), (II) or (III) or an end group B (Si-bound) or D (O-bound), B denotes a group —OH, —O—Si($CH_3$)$_3$, —O—Si($CH_3$)$_2$OH, —O—Si($CH_3$)$_2$OCH$_3$; D denotes a group —H; —Si($CH_3$)$_3$, —Si($CH_3$)$_2$OH, —Si($CH_3$)$_2$OCH$_3$; A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH, and n, m and o denote integers between 1 and 1000.

A hair treatment agent including at least one 4-morpholinomethyl-substituted silicone of formula (IV)

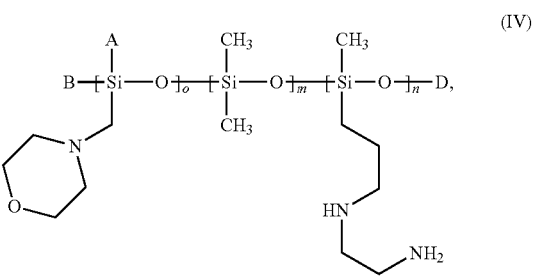

in which A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH, B denotes a group —OH, —O—Si($CH_3$)$_3$, —O—Si($CH_3$)$_2$OH, —O—Si($CH_3$)$_2$OCH$_3$, D denotes a group —H; —Si($CH_3$)$_3$, —Si($CH_3$)$_2$OH, —Si($CH_3$)$_2$OCH$_3$, and n, m and o denote integers between 1 and 1000, the siloxane units m, n and o being present in random distribution.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present invention firstly provides hair treatment agents including at least one 4-morpholinomethyl-substituted silicone, which in each case comprises at least one of the structural units of formulae (I), (II) and (III)

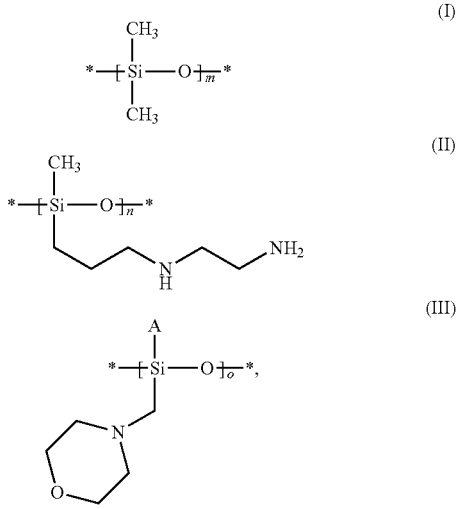

where
* denotes a bond to one of the structural units (I), (II) or (III) or denotes an end group B (Si-bound) or D (O-bound),
B denotes a group —OH, —O—Si(CH$_3$)$_3$, —O—Si(CH$_3$)$_2$OH, —O—Si(CH$_3$)$_2$OCH$_3$,
D denotes a group —H; —Si(CH$_3$)$_3$, —Si(CH$_3$)$_2$OH, —Si(CH$_3$)$_2$OCH$_3$,
A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH,
m and o denote integers between 1 and 1000.

Hair treatment agents within the meaning of the present invention are, for example, hair shampoos, hair conditioners, conditioning shampoos, hairsprays, hair rinses, deep conditioners, hair masques, hair tonics, permanent wave fixing solutions, hair coloring shampoos, hair coloring agents, hair fixatives, hair setting compositions, hair styling preparations, blow-drying lotions, styling mousses, hair gels, hair waxes or combinations thereof. In view of the fact that men are often reluctant to use several different agents and/or several application steps, agents according to the invention are preferably those agents that a man uses in any case. Preferred agents according to the invention are therefore shampoos, conditioning agents or hair tonics.

The agents according to the invention include as a first essential ingredient at least one 4-morpholinomethyl-substituted silicone. This silicone comprises in each case at least one of the structural units of formulae (I), (II) and (III).

The structural units of formulae (I), (II) and (III) can be present in the molecule in random distribution, but the silicones used according to the invention can also be block copolymers comprising blocks of the individual structural units, in which case the blocks can again be present in random distribution.

The * on the free valencies of the structural units (I), (II) or (III) here denotes a bond to one of the structural units (I), (II) or (III) or an end group B (Si-bound) or D (O-bound).

The silicones used according to the invention can be trimethylsilyl-terminated at both ends (D=—Si(CH$_3$)$_3$, B=—O—Si(CH$_3$)$_3$), but they can also be dimethylsilylhydroxy- or dimethylsilylmethoxy-terminated at one or both ends. Particularly preferably used silicones within the framework of the present invention comprise at least one terminal dimethylsilylhydroxy group, i.e. are selected from silicones where the following meanings apply:
B=—O—Si(CH$_3$)$_2$OH and D=—Si(CH$_3$)$_3$
B=—O—Si(CH$_3$)$_2$OH and D=—Si(CH$_3$)$_2$OH
B=—O—Si(CH$_3$)$_2$OH and D=—Si(CH$_3$)$_2$OCH$_3$
B=—O—Si(CH$_3$)$_3$ and D=—Si(CH$_3$)$_2$OH
B=—O—Si(CH$_3$)$_2$OCH$_3$ and D=—Si(CH$_3$)$_2$OH.

These silicones lead to vast improvements in the hair properties of hair treated with the agents according to the invention, and in particular to a significant reduction in the contact angle.

In the structural unit (III), the residue A can denote
a structural unit (I), (II) or (III) bound by an —O— or
an oligomeric or polymeric residue including structural units of formulae (I), (II) or (III) bound by an —O—
or half of a connecting O atom to a structural unit (III) or —OH.

In the first case, the structural unit (III) becomes one of the structural units (IIIa), (IIIb) or (IIIc):

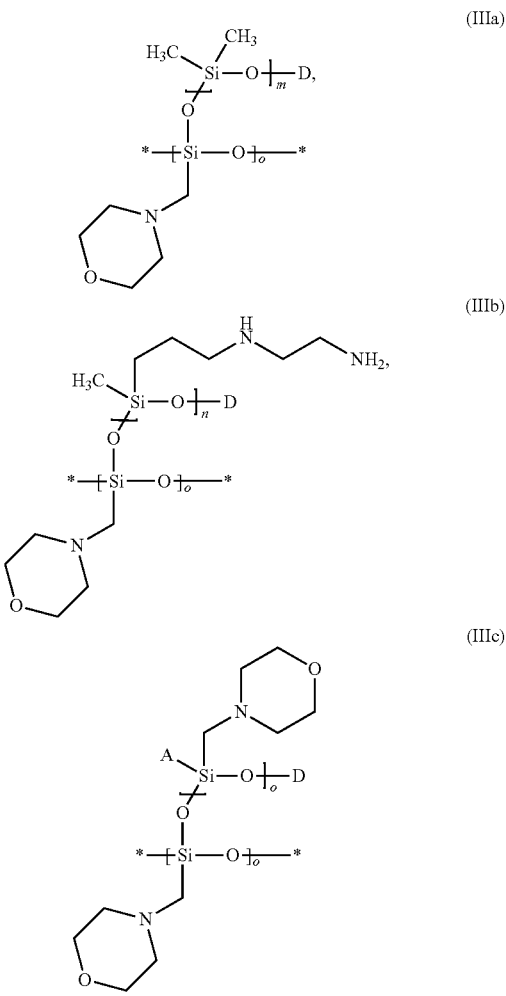

with m=n=o=1 and A and D respectively as defined above.

In the second case, in the above-mentioned formulae (IIIa), (IIIb) and (IIIc), the indices m, n and o can denote integers between 2 and 1000. However, the second case also covers oligomeric or polymeric residues that include at least two different structural units of formulae (I), (II) or (III), as shown in formula (IIId):

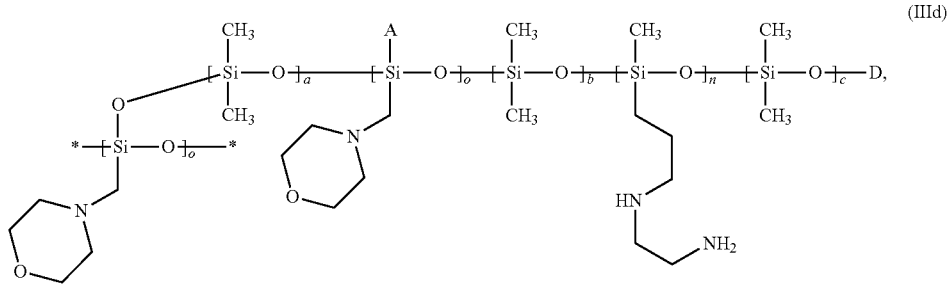

in which a, b and c denote integers between 0 and 1000, with the proviso that a+b+c>0, and also n and o denote integers between 1 and 1000.

In the third case, A denotes half of a connecting O atom to a structural unit (III) (illustrated in structural unit (IIIe) or —OH (illustrated in structural unit (IIIf)

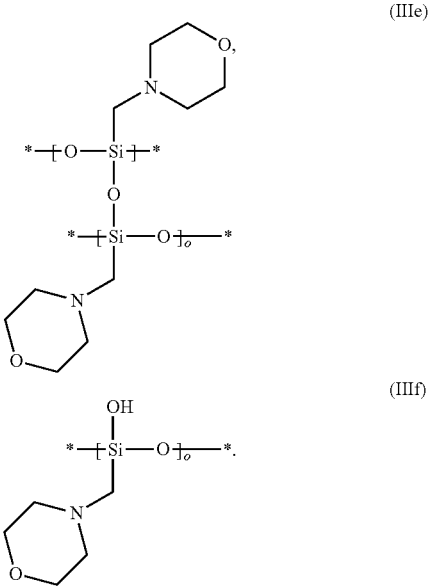

The present invention also provides hair treatment agents including at least one 4-morpholinomethyl-substituted silicone of formula (IV)

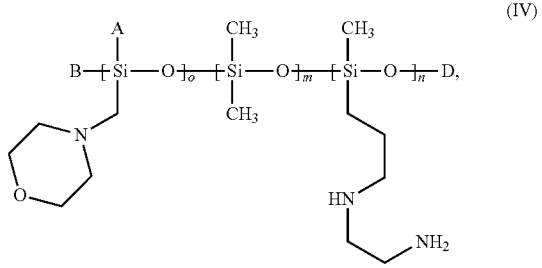

in which

A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH, B denotes a group —OH, —O—Si(CH$_3$)$_3$, —O—Si(CH$_3$)$_2$OH, —O—Si(CH$_3$)$_2$OCH$_3$, D denotes a group —H; —Si(CH$_3$)$_3$, —Si(CH$_3$)$_2$OH, —Si(CH$_3$)$_2$OCH$_3$, n, m and o denote integers between 1 and 1000, the siloxane units m, n and o being present in random distribution.

The silicones used according to the invention represented by formula (IV) can also be trimethylsilyl-terminated at both ends (D=—Si(CH$_3$)$_3$, B=—O—Si(CH$_3$)$_3$), but they can also be dimethylsilylhydroxy- or dimethylsilylmethoxy-terminated at one or both ends. Particularly preferably used silicones within the framework of the present invention comprise at least one terminal dimethylsilylhydroxy group, i.e. are selected from silicones in which the following meanings apply:

B=—O—Si(CH$_3$)$_2$OH and D=—Si(CH$_3$)$_3$
B=—O—Si(CH$_3$)$_2$OH and D=—Si(CH$_3$)$_2$OH
B=—O—Si(CH$_3$)$_2$OH and D=—Si(CH$_3$)$_2$OCH$_3$
B=—O—Si(CH$_3$)$_3$ and D=—Si(CH$_3$)$_2$OH
B=—O—Si(CH$_3$)$_2$OCH$_3$ and D=—Si(CH$_3$)$_2$OH.

These silicones lead to vast improvements in the hair properties of hair treated with the agents according to the invention, and in particular to a significant reduction in the contact angle.

In formula (IV) too, the residue A can denote a structural unit (I), (II) or (III) bound by an —O— or an oligomeric or polymeric residue including structural units of formulae (I), (II) or (III) bound by an —O— or half of a connecting O atom to a structural unit (III) or —OH.

In the same way as for the statements regarding structural unit (III), formula (IV) is therefore stated more precisely as one of formulae (IVa), (IVb), (IVc), (IVd), (IVe) or (IVf) as disclosed in the priority document on pages 6 to 8.

As already mentioned, the structural units of formulae (I), (II) and (III) and the siloxane units m, n and o respectively can preferably be present in random distribution. Preferred hair treatment agents according to the invention include at least one 4-morpholinomethyl-substituted silicone of formula (V)

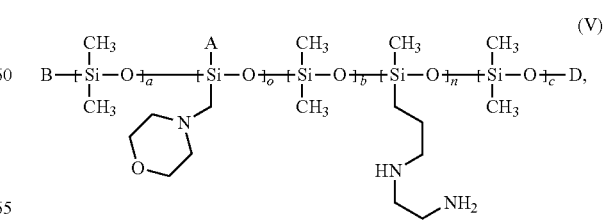

in which
A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH, B denotes a group —OH, —O—Si(CH$_3$)$_3$, —O—Si(CH$_3$)$_2$OH, —O—Si(CH$_3$)$_2$OCH$_3$, D denotes a group —H; —Si(CH$_3$)$_3$, —Si(CH$_3$)$_2$OH, —Si(CH$_3$)$_2$OCH$_3$, a, b and c denote integers between 0 and 1000, with the proviso that a+b+c>0 n and o denote integers between 1 and 1000.

Structural formula (V) is intended to clarify, in comparison with formula (IV), that the siloxane groups n and o do not necessarily have to be bound directly to an end grouping B or D. Rather, in preferred formulae (V), a>0 or b>0 applies and in particularly preferred formulae (V) a>0 and b>0, i.e. the terminal grouping B or D is preferably bound to a dimethylsiloxy grouping. In formula (V) too, the siloxane units a, b, c, n and o are preferably randomly distributed.

The silicones used according to the invention represented by formula (V) can also be trimethylsilyl-terminated at both ends (D═—Si(CH$_3$)$_3$ B═—O—Si(CH$_3$)$_3$), but they can also be dimethylsilylhydroxy- or dimethylsilylmethoxy-terminated at one or both ends. Particularly preferably used silicones within the framework of the present invention comprise at least one terminal dimethylsilylhydroxy group, i.e. are selected from silicones, in which the following meanings apply:

B═—O—Si(CH$_3$)$_2$OH and D═—Si(CH$_3$)$_3$
B═—O—Si(CH$_3$)$_2$OH and D═—Si(CH$_3$)$_2$OH
B═—O—Si(CH$_3$)$_2$OH and D═—Si(CH$_3$)$_2$OCH$_3$
B═—O—Si(CH$_3$)$_3$ and D═—Si(CH$_3$)$_2$OH
B═—O—Si(CH$_3$)$_2$OCH$_3$ and D═—Si(CH$_3$)$_2$OH.

These silicones lead to vast improvements in the hair properties of the hair treated with the agents according to the invention, and in particular to a significant reduction in the contact angle.

In formula (V) too, the residue A can denote
a structural unit (I), (II) or (III) bound by an —O— or
an oligomeric or polymeric residue including structural units of formulae (I), (II) or (III) bound by an —O—
or half of a connecting O atom to a structural unit (III) or —OH.

In the same way as for the statements regarding structural unit (III) and formula (IV) respectively, formula (V) is therefore stated more precisely as one of formulae (Va), (Vb), (Vc), (Vd), (Ve) or (Vf):

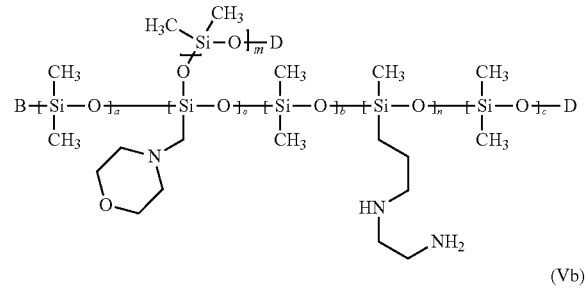

(Va)

(Vb)

(Vc)

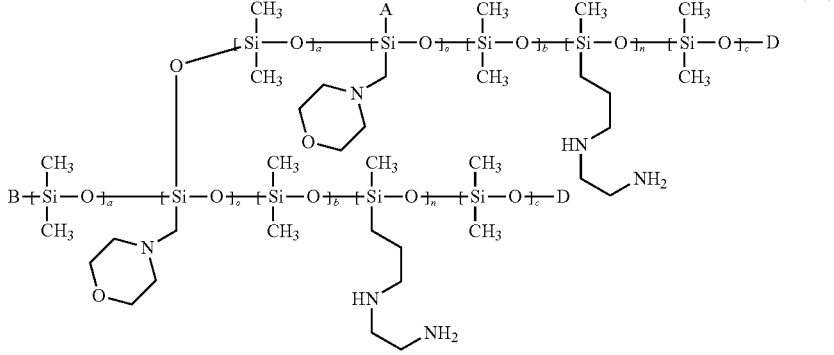

(Vd)

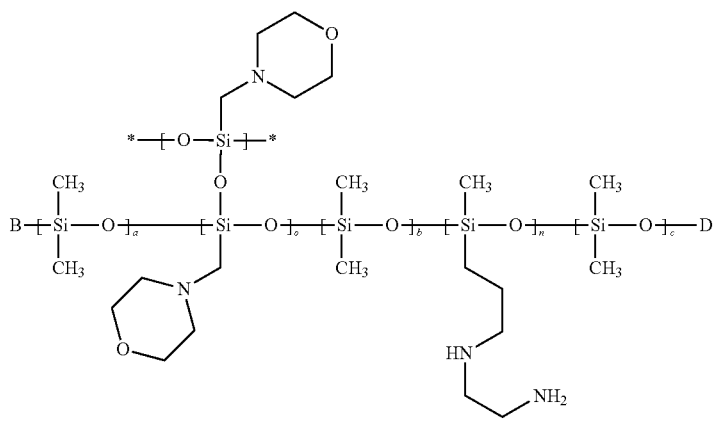

(Ve)

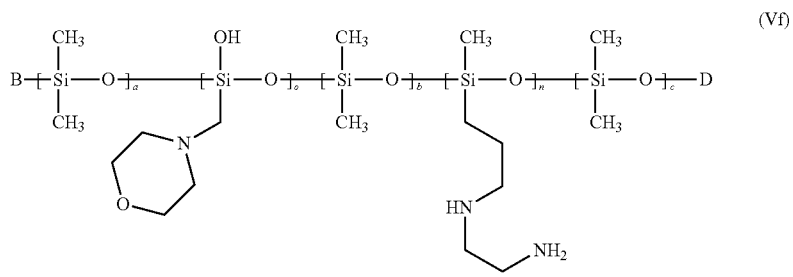

(Vf)

The structural unit (III) and the siloxane units o respectively in formulae (IV) and (V) can form nido or partial cage structures via the group A if A denotes half of a connecting O atom to a structural unit (III). Hair treatment agents according to the invention which include silicones with corresponding 4-morpholinomethyl-substituted silsequioxane partial structures are preferred according to the invention, since these silicones lead to greatly improved combability and dramatically reduced contact angles.

Preferred hair treatment agents according to the invention are accordingly characterized in that they include at least one 4-morpholinomethyl-substituted silicone, which comprises structural units of formula (VI)

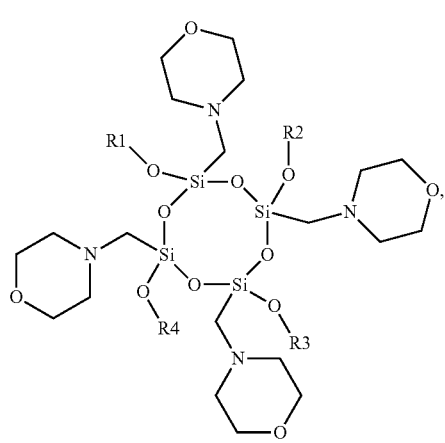

(VI)

in which

R1, R2, R3 and R4 independently of one another denote —H, —CH$_3$, a group D, a structural unit (I), (II) or (III) or an oligomeric or polymeric residue including structural units of formulae (I), (II) or (III) or two of the residues R1, R2, R3 and R4 denote a structural unit —Si(R6)(R5)- with R5=—CH$_3$ or a structural unit of formula (I) or (II) or (III) or an oligomeric or polymeric residue including structural units of formulae (I), (II) or (III)

R6=—OH, —CH$_3$ or a structural unit of formula (I) or (II) or (III) or an oligomeric or polymeric residue including structural units of formulae (I), (II) or (III).

In preferred silicones of formula (VI) at least one of the residues R1, R2, R3 or R4 denotes an oligomeric or polymeric residue including structural units of formulae (I), (II) or (III).

In further preferred silicones of formula (VI), at least one of the residues R1, R2, R3 or R4 denotes an oligomeric or polymeric residue including structural units of formulae (I) and (II). In still further preferred silicones of formula (VI) at least one of the residues R1, R2, R3 or R4 denotes an oligomeric or polymeric residue including structural units of formulae (I) and (II) and (III).

Preferably at least one of the residues R1, R2, R3 or R4 denotes a —[—Si(CH$_3$)$_2$—O]$_m$— grouping, i.e. an oligomer or polymer of the structural unit (I). In addition, the structural unit (II) or an oligomer or polymer thereof is preferably never bound in the molecule alone but always in random distribution with other structural units of formula (I) as one of the residues R1, R2, R3 or R4.

Preferred silicones of formula (VI) can be described by the formula (VI a)

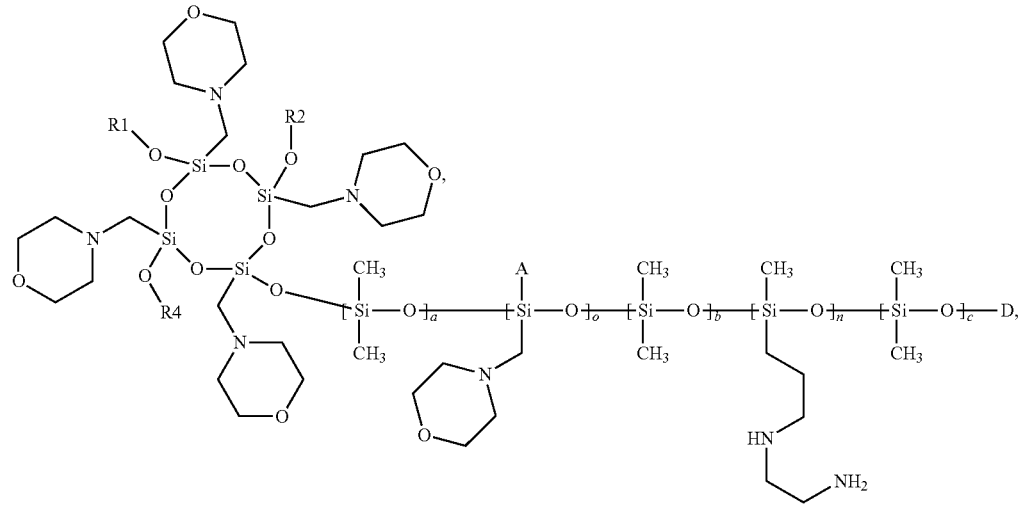

in which
R1, R2 and R4 independently of one another denote —H, —CH$_3$, a group D, a structural unit (I), (II) or (III) or an oligomeric or polymeric residue including structural units of formulae (I), (II) or (III) or two of the residues R1, R2 and R4 denote a structural unit —Si(R6)(R5)- with
R5=—CH$_3$ or a structural unit of formula (I) or (II) or (III) or an oligomeric or polymeric residue including structural units of formulae (I), (II) or (III)
R6=—OH, —CH$_3$, or a structural unit of formula (I) or (II) or (III) or an oligomeric or polymeric residue including structural units of formulae (I), (II) or (III), A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH, D denotes a group —H; —Si(CH$_3$)$_3$, —Si(CH$_3$)$_2$OH, —Si(CH$_3$)$_2$OCH$_3$, a, b and c denote integers between 0 and 1000, with the proviso that a+b+c>0 n and o denote integers between 1 and 1000.

Further preferred silicones of formula (VI) can be described by the formula (VI b)

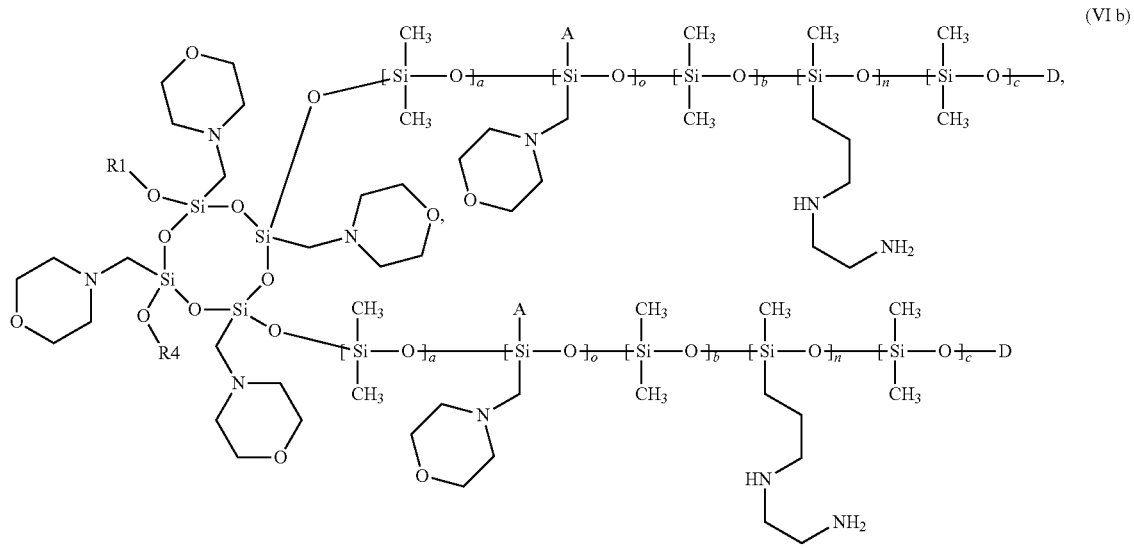

in which the residues and indices are as defined above.

Particularly preferred silicones of formula (VI) can be described by the formula (VI c)

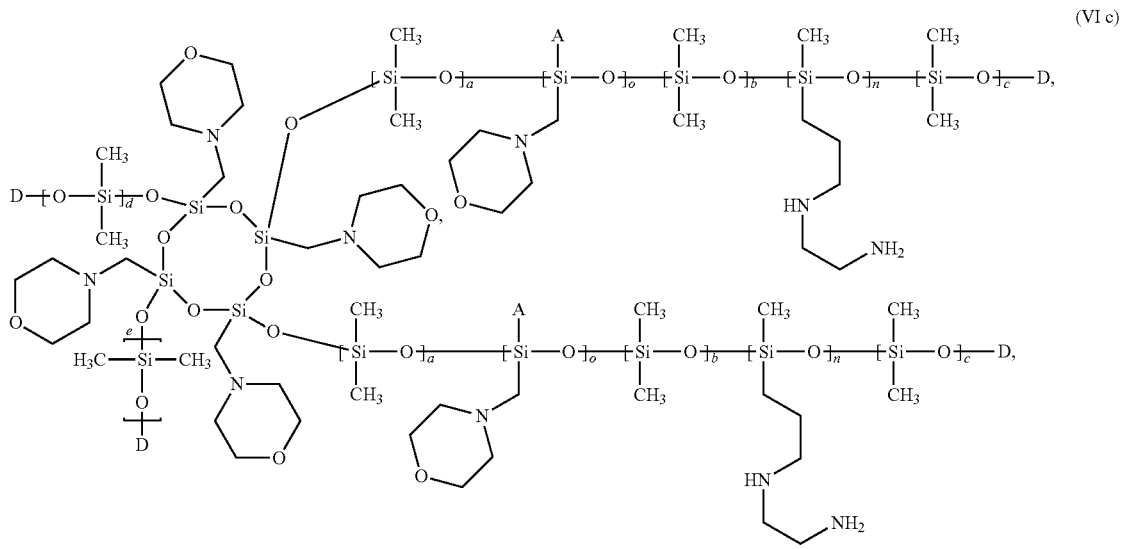

(VI c)

in which the residues and indices are as defined above and the indices d and e denote integers between 0 and 1000.

In formulae (VI a), (VI b) and (VI c) at least one of the groupings D preferably denotes —Si(CH$_3$)$_2$OH.

The silsequioxane structures can be even more marked in the silicones used according to the invention. Which reinforces the advantageous effects. Particularly preferred hair treatment agents according to the invention are characterized in that they include at least one 4-morpholinomethyl-substituted silicone, which comprises structural units of formula (VII)

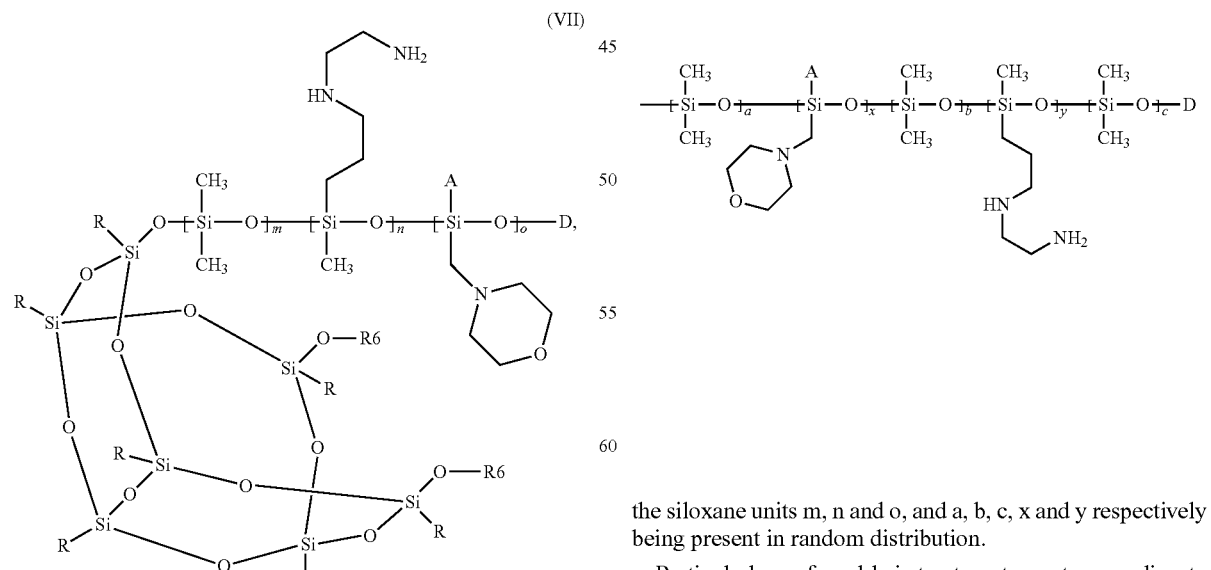

(VII)

in which

A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH, D denotes a group —H; —Si(CH$_3$)$_3$, —Si(CH$_3$)$_2$OH, —Si(CH$_3$)$_2$OCH$_3$, R denotes a residue 4-morpholinomethyl, R6 denotes —H or the grouping the siloxane units m, n and o, and a, b, c, x and y respectively being present in random distribution.

Particularly preferred hair treatment agents according to the invention include at least one silicone of the following formula (VII a)

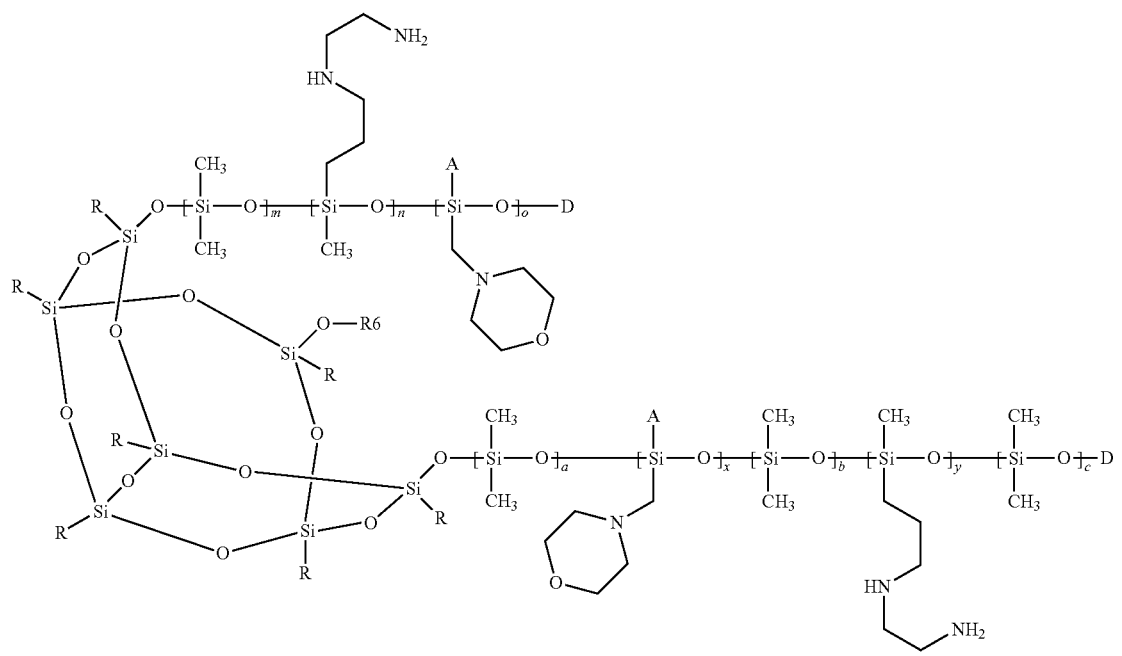

(VII a) with the definitions as for formula (VII).

Most particularly preferred hair treatment agents according to the invention include at least one silicone of the following formula (VII b)

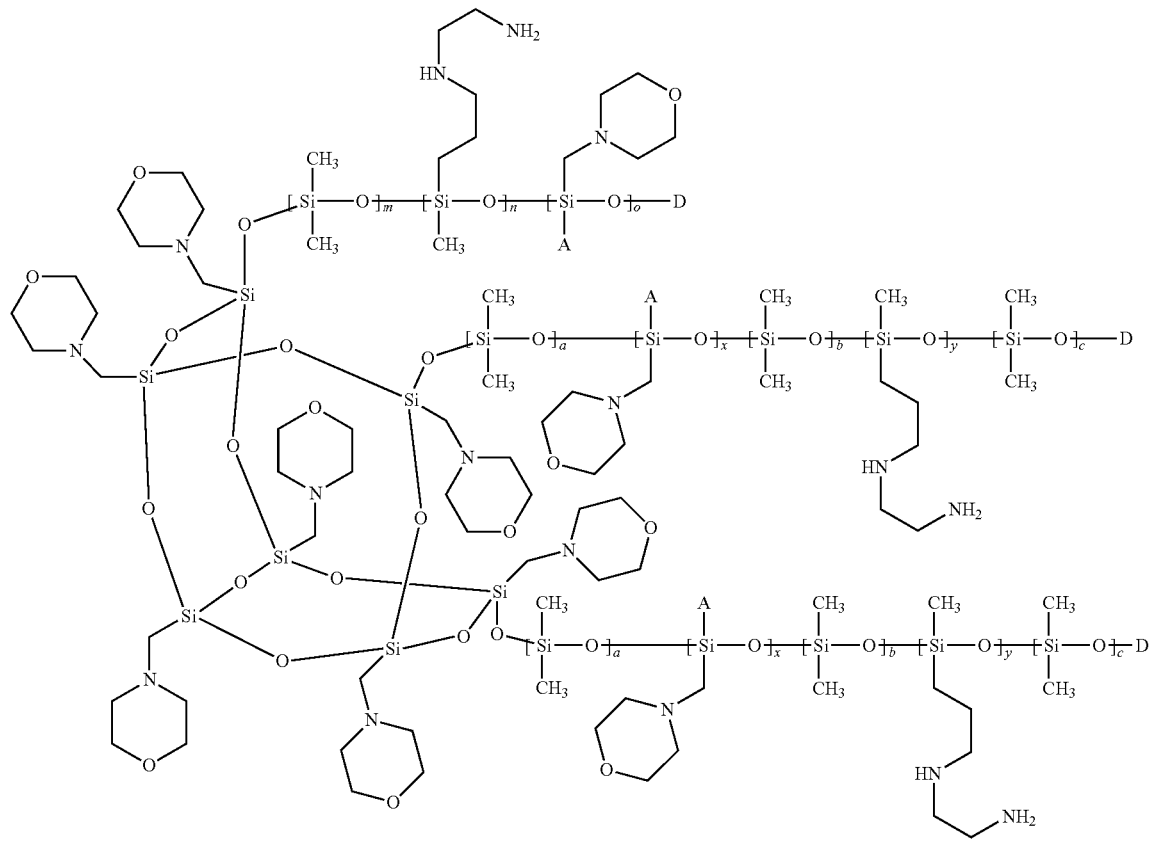

(VII b) with the definitions as for formula (VII).

In formulae (VII), (VII a) and (VII b), the bridging oxygen atoms between the morpholinomethyl-substituted silicon atoms can also be extended by a —[—Si(CH$_3$)$_2$—O]$_m$ grouping, i.e. an oligomer or polymer of structural unit (I). Corresponding hair treatment agents according to the invention, including at least one 4-morpholinomethyl-substituted silicone, which comprises structural units of formula (VIII)

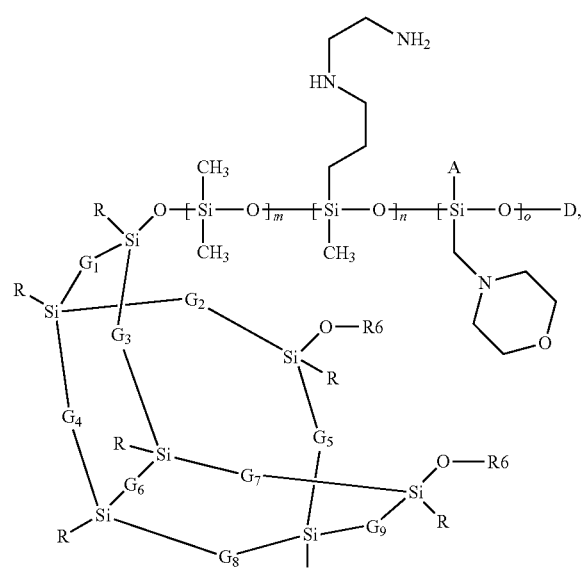

(VIII)

in which
A denotes a structural unit (I), (II) or (III) bound by an —O— or an oligomeric or polymeric residue including structural units of formulae (I), (II) or (III) bound by an —O— or half of a connecting O atom to a structural unit (III), or denotes —OH, D denotes a group —H; —Si(CH$_3$)$_3$, —Si(CH$_3$)$_2$OH, —Si(CH$_3$)$_2$OCH$_3$, G1 to G9 independently of one another denote —O— or a group —[—Si(CH$_3$)$_2$—O]$_m$— with m=1 to 200, R denotes a residue 4-morpholinomethyl, R6 denotes —H or the grouping

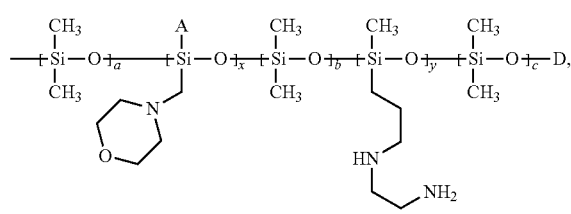

the siloxane units m, n and o, and a, b, c, x and y respectively being present in random distribution.

Particularly preferred hair treatment agents according to the invention include at least one silicone of the following formula (VIII a)

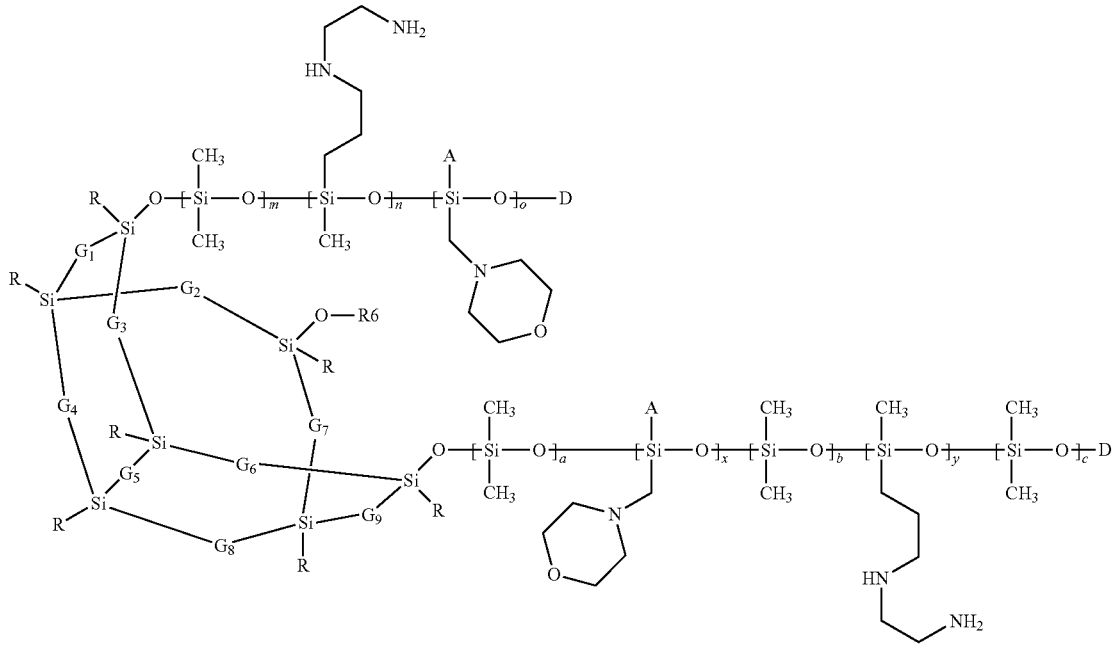

(VIII a) with the definitions as for formula (VIII).

Most particularly preferred hair treatment agents according to the invention include at least one silicone of the following formula (VIII b)

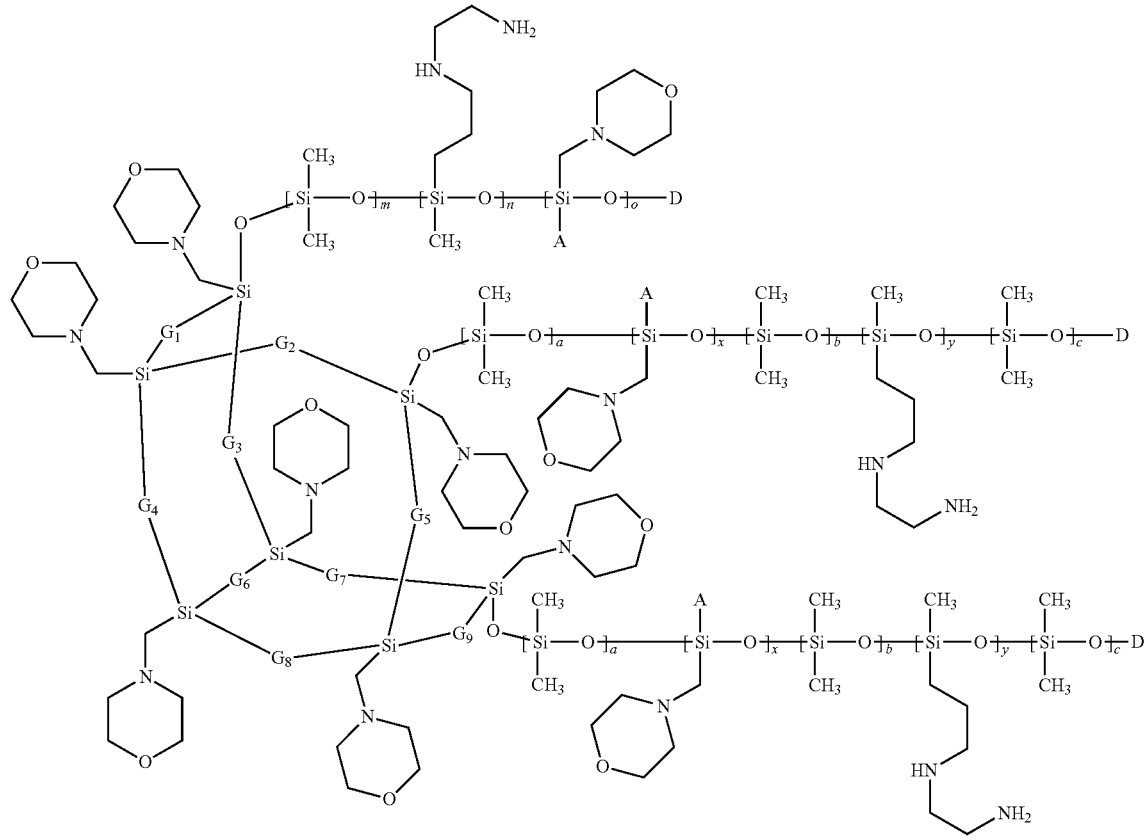

(VIII b) with the definitions as for formula (VIII).

Irrespective of which special 4-morpholinomethyl-substituted silicone is used in the hair treatment agents according to the invention, agents according to the invention including a 4-morpholinomethyl-substituted silicone in which more than 50 mole % of the structural units are dimethylsiloxy units, i.e. in which the structural unit (I) makes up at least half of all structural units in the silicone used, are preferred.

In other words, silicones are preferred in which m>(n+o) and (a+b+c)>(n+o) respectively apply.

Still further preferred hair treatment agents include a 4-morpholinomethyl-substituted silicone in which more than 90 mole % of the structural units are dimethylsiloxy units, i.e. in which the structural unit (I) makes up at least nine tenths of all structural units in the silicone used.

In other words, silicones are preferred in which m>10(n+o) and (a+b+c)>10(n+o) respectively apply.

Still further preferred hair treatment agents include a 4-morpholinomethyl-substituted silicone in which more than 98 mole % of the structural units are dimethylsiloxy units, i.e. in which the structural unit (I) makes up at least ninety-eight hundredths of all structural units in the silicone used.

In other words, silicones are preferred in which m>50(n+o) and (a+b+c)>50(n+o) respectively apply.

Still further preferred hair treatment agents include a 4-morpholinomethyl-substituted silicone in which more than 98.5 mole % of the structural units are dimethylsiloxy units, i.e. in which the structural unit (I) makes up at least nine hundred and eight-five thousandths of all structural units in the silicone used.

In other words, silicones are preferred in which m>75(n+o) and (a+b+c)>75(n+o) respectively apply.

Still further preferred hair treatment agents include a 4-morpholinomethyl-substituted silicone in which more than 99 mole % of the structural units are dimethylsiloxy units, i.e. in which the structural unit (I) makes up at least nine tenths of all structural units in the silicone used.

In other words, silicones are preferred in which m>100(n+o) and (a+b+c)>100(n+o) respectively apply.

In summary, preferred hair treatment agents according to the invention are characterized in that they include at least one 4-morpholinomethyl-substituted silicone, in which m>(n+o) and (a+b+c)>(n+o) respectively, preferably
m>10(n+o) and (a+b+c)>10(n+o) respectively, particularly preferably
m>50(n+o) and (a+b+c)>50(n+o) respectively, more preferably
m>75(n+o) and (a+b+c)>75(n+o) respectively and in particular
m>100(n+o) and (a+b+c)>100(n+o) respectively apply.

The 4-morpholinomethyl-substituted silicone(s) can be used in varying quantities depending on the intended application of the agents according to the invention. Preferred hair treatment agents according to the invention are characterized in that they include—based on their weight—0.00001 to 10 wt. %, preferably 0.0001 to 7.5 wt. %, particularly preferably 0.001 to 5 wt. %, more preferably 0.01 to 3 wt. % and in particular 0.1 to 1 wt. % 4-morpholinomethyl-substituted silicone(s).

It has been shown that the action of the silicones used according to the invention can be increased still further if specific nonionic components are also used in the agents according to the invention. Moreover, these nonionic components have positive effects on the storage stability of the agents according to the invention. Nonionic components that are particularly suitable here are ethoxylates of decanol, undecanol, dodecanol, tridecanol etc. Ethoxylated tridecanols, which are incorporated into the agents according to the invention with particular preference, have proved particularly suitable. Particularly preferred hair treatment agents according to the invention include—based on their weight—0.00001 to 5 wt. %, preferably 0.0001 to 3.5 wt. %, particularly preferably 0.001 to 2 wt. %, more preferably 0.01 to 1 wt. % and in particular 0.1 to 0.5 wt. % branched, ethoxylated tridecanol (INCI name: Trideceth-5) or α-isotridecyl-ω-hydroxy polyglycol ether (INCI name: Trideceth-10) or mixtures thereof.

The agents according to the invention include other essential ingredients, depending on their intended application. Cleaning or care compositions, such as for example shampoos or conditioners, include at least one surfactant, surface-active substances being referred to as surfactants or emulsifiers depending on the area of application and being selected from anionic, cationic, zwitterionic, ampholytic and nonionic surfactants and emulsifiers.

Preferred hair treatment agents according to the invention are characterized in that they include—based on their weight—0.5 to 70 wt. %, preferably 1 to 60 wt. % and in particular 5 to 25 wt. % anionic and/or nonionic and/or cationic and/or amphoteric surfactant(s).

Suitable as anionic surfactants and emulsifiers for the compositions according to the invention are all anionic surface-active substances that are suitable for use on the human body. These are characterized by a water-solubilizing anionic group, such as e.g. a carboxylate, sulfate, sulfonate or phosphate group, and a lipophilic alkyl group with about 8 to 30 C atoms. In addition, glycol or polyglycol ether groups, ester, ether and amide groups as well as hydroxyl groups can be included in the molecule. Examples of suitable anionic surfactants and emulsifiers are, in each case in the form of the sodium, potassium and ammonium salts as well as the mono-, di- and trialkanolammonium salts with 2 to 4 C atoms in the alkanol group, linear and branched fatty acids with 8 to 30 C atoms (soaps),
ether carboxylic acids of the formula R—O—(CH$_2$—CH$_2$O)$_x$—CH$_2$—COOH, in which R is a linear alkyl group with 8 to 30 C atoms and x=0 or 1 to 16,
acyl sarcosides with 8 to 24 C atoms in the acyl group,
acyl taurides with 8 to 24 C atoms in the acyl group,
acyl isethionates with 8 to 24 C atoms in the acyl group,
linear alkanesulfonates with 8 to 24 C atoms,
linear alpha-olefin sulfonates with 8 to 24 C atoms,
alpha-sulfo fatty acid methyl esters of fatty acids with 8 to 30 C atoms,
acylglutamates of formula (I),

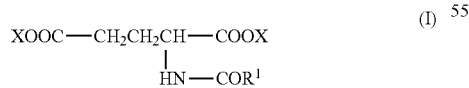

(I)

in which R$^1$CO denotes a linear or branched acyl residue with 6 to 22 carbon atoms and 0, 1, 2 or 3 double bonds and X denotes hydrogen, an alkali metal and/or alkaline earth metal, ammonium, alkylammonium, alkanolammonium or glucammonium, for example acylglutamates, which are derived from fatty acids with 6 to 22, preferably 12 to 18 carbon atoms, such as for example C$_{12/14}$ or C$_{12/18}$ coconut fatty acid, lauric acid, myristic acid, palmitic acid and/or stearic acid, in particular sodium N-cocoyl and sodium N-stearoyl L-glutamate,
esters of a hydroxy-substituted di- or tricarboxylic acid of general formula (II),

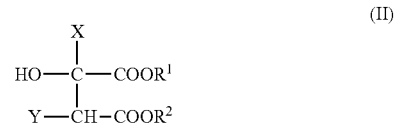

(II)

in which X=H or a —CH$_2$COOR group, Y=H or —OH on condition that Y=H if X=—CH$_2$COOR, R, R$^1$ and R$^2$ independently of one another signify a hydrogen atom, an alkali metal or alkaline earth metal cation, an ammonium group, the cation of an ammonium organic base or a residue Z, which originates from a polyhydroxylated organic compound, which are selected from the group of the etherified (C$_6$-C$_{18}$) alkyl polysaccharides with 1 to 6 monomeric saccharide units and/or the etherified aliphatic (C$_6$-C$_{16}$) hydroxyalkyl polyols with 2 to 16 hydroxyl residues, with the proviso that at least one of the groups R, R$^1$ or R$^2$ is a residue Z,
esters of sulfosuccinic acid or sulfosuccinates of general formula (III),

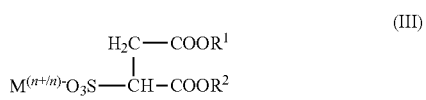

(III)

in which M$^{(n+/n)}$ represents for n=1 a hydrogen atom, an alkali metal cation, an ammonium group or the cation of an ammonium organic base and for n=2 an alkaline earth metal cation, and R$^1$ and R$^2$ independently of one another signify a hydrogen atom, an alkali metal or alkaline earth metal cation, an ammonium group, the cation of an ammonium organic base or a residue Z, which originates from a polyhydroxylated organic compound, which is selected from the group of the etherified (C$_6$-C$_{18}$) alkyl polysaccharides with 1 to 6 monomeric saccharide units and/or the etherified aliphatic (C$_6$-C$_{16}$) hydroxyalkyl polyols with 2 to 16 hydroxyl residues, with the proviso that at least one of the groups R$^1$ or R$^2$ is a residue Z, sulfosuccinic acid mono- and dialkyl esters with 8 to 24 C atoms in the alkyl group and sulfosuccinic acid monoalkylpolyoxyethyl esters with 8 to 24 C atoms in the alkyl group and 1 to 6 oxyethyl groups,
alkyl sulfates and alkyl polyglycol ether sulfates of the formula R—(O—CH$_2$—CH$_2$)$_x$—OSO$_3$H, in which R is a preferably linear alkyl group with 8 to 30 C atoms and x=0 or 1-12,
mixed surface-active hydroxysulfonates according to DE-A-37 25 030,
esters of tartaric acid and citric acid with alcohols, which represent addition products of about 2-15 molecules of ethylene oxide and/or propylene oxide to C$_8$-$_{22}$ fatty alcohols,
alkyl and/or alkenyl ether phosphates,
sulfated fatty acid alkylene glycol esters,
monoglyceride sulfates and monoglyceride ether sulfates.

Preferred anionic surfactants and emulsifiers are acylglutamates, acyl isethionates, acyl sarcosinates and acyl taurates, in each case with a linear or branched acyl residue with 6 to 22 carbon atoms and 0, 1, 2 or 3 double bonds, which is selected in particularly preferred embodiments from an octanoyl, decanoyl, lauroyl, myristoyl, palmitoyl and stearoyl residue, esters of tartaric acid, citric acid or succinic acid or the salts of these acids with alkylated glucose, in particular the products with the INCI name Disodium Coco-Glucoside Citrate, Sodium Coco-Glucoside Tartrate and Disodium Coco-Glucoside Sulfosuccinate, alkyl polyglycol ether sulfates and ether carboxylic acids with 8 to 18 C atoms in the alkyl group and up to 12 ethoxy groups in the molecule, sulfosuccinic acid mono- and dialkyl esters with 8 to 18 C atoms in the alkyl group and sulfosuccinic acid monoalkylpolyoxyethyl esters with 8 to 18 C atoms in the alkyl group and 1 to 6 ethoxy groups.

Those surface-active compounds carrying at least one quaternary ammonium group and at least one —COO$^{(-)}$— or —SO$_3^{(-)}$ group in the molecule are referred to as zwitterionic surfactants and emulsifiers. Particularly suitable zwitterionic surfactants and emulsifiers are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethyl imidazolines with 8 to 18 C atoms in the alkyl or acyl group in each case, as well as cocoacylaminoethyl-hydroxyethylcarboxymethyl glycinate. A preferred zwitterionic surfactant is the fatty acid amide derivative known by the INCI name Cocamidopropyl Betaine.

Further preferred anionic surfactants are alkyl sulfates, alkyl polyglycol ether sulfates and ether carboxylic acid salts with 10 to 18 C atoms in the alkyl group and up to 12 glycol ether groups in the molecule and sulfosuccinic acid mono- and dialkyl esters with 8 to 18 C atoms in the alkyl group and sulfosuccinic acid monoalkylpolyoxyethyl esters with 8 to 18 C atoms in the alkyl group and 1 to 6 oxyethyl groups.

Particularly preferred anionic surfactants are the alkali or ammonium salts of lauryl ether sulfate with a degree of ethoxylation of 2 to 4 EQ.

Particularly preferred hair treatment agents according to the invention are characterized in that they include—based on their weight—0.1 to 20 wt. %, preferably 0.25 to 17.5 wt. % and in particular 5 to 15 wt. % anionic surfactant(s), particularly preferably fatty alcohol ether sulfates of the formula

H$_3$C—(CH$_2$)$_n$—(OCH$_2$CH$_2$)$_k$—OSO$_3^-$M$^+$ in which n denotes values of 5 to 21, preferably of 7 to 19, particularly preferably of 9 to 17 and in particular of 11 to 13 and k denotes values of 1, 2, 3, 4, 5, 6, 7, 8, 9 or 10, preferably 1, 2 or 3 and in particular 2, and M denotes a cation from the group Na$^+$, K$^+$ NH$_4^+$, ½Mg$^{2+}$, ½ Zn$^{2+}$, preferably Na$^+$.

Those surface-active compounds carrying at least one quaternary ammonium group and at least one —COO$^{(-)}$— or —SO$_3^{(-)}$ group in the molecule are referred to as zwitterionic surfactants and emulsifiers. Particularly suitable zwitterionic surfactants and emulsifiers are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethyl imidazolines with 8 to 18 C atoms in the alkyl or acyl group in each case, as well as cocoacylaminoethyl-hydroxyethylcarboxymethyl glycinate. A preferred zwitterionic surfactant is the fatty acid amide derivative known by the INCI name Cocamidopropyl Betaine.

Ampholytic surfactants and emulsifiers are understood to be those surface-active compounds which, apart from a C$_8$-C$_{24}$ alkyl or acyl group, include at least one free amino group and at least one —COOH— or —SO$_3$H group and are capable of forming internal salts. Examples of suitable ampholytic surfactants are N-alkylglycines, N-alkylaminopropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids with in each case about 8 to 24 C atoms in the alkyl group. Particularly preferred ampholytic surfactants are N-cocoalkylaminopropionate, cocoacylaminoethylaminopropionate and C$_{12}$-C$_{18}$ acylsarcosine.

Particularly preferred hair treatment agents according to the invention are characterized in that they include amphoteric surfactant(s) from the groups of the N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids with in each case about 8 to 24 C atoms in the alkyl group, alkylaminoacetic acids with in each case about 8 to 24 C atoms in the alkyl group, N-cocoalkylaminopropionate, cocoacylaminoethylaminopropionate, C$_{12}$-C$_{18}$ acylsarcosine, N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, 2-alkyl-3-carboxymethyl-3-hydroxyethyl imidazolines with in each case 8 to 18 C atoms in the alkyl or acyl group, cocoacylaminoethylhydroxyethylcarboxymethyl glycinate, the compounds known by the INCI name Cocamidopropyl Betaine, the compounds known by the INCI name Disodium Cocoamphodiacetate, preferred agents including the amphoteric surfactant(s) in quantities of 0.5 to 9 wt. %, preferably of 0.75 to 8 wt. % and in particular of 1 to 7.5 wt. %, based in each case on the overall agent.

Particularly preferred hair treatment agents include as amphoteric surfactants betaines of the formula (Bet-I)

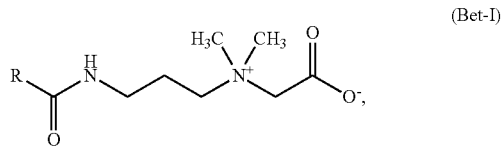

(Bet-I)

in which R denotes a straight-chained or branched, saturated or mono- or polyunsaturated alkyl or alkenyl residue with 8 to 24 carbon atoms.

These surfactants are referred to according to INCI nomenclature as Amidopropyl Betaines, the representatives derived from coconut fatty acids being preferred and being referred to as Cocamidopropyl Betaines. Particularly preferably according to the invention, surfactants of the formula (Bet-I) are used, which are a mixture of the following representatives:

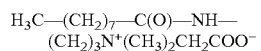

H$_3$C—(CH$_2$)$_7$—C(O)—NH—
 (CH$_2$)$_3$N$^+$(CH$_3$)$_2$CH$_2$COO$^-$

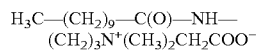

H$_3$C—(CH$_2$)$_9$—C(O)—NH—
 (CH$_2$)$_3$N$^+$(CH$_3$)$_2$CH$_2$COO$^-$

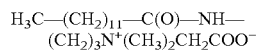

H$_3$C—(CH$_2$)$_{11}$—C(O)—NH—
 (CH$_2$)$_3$N$^+$(CH$_3$)$_2$CH$_2$COO$^-$

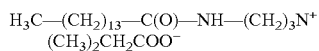
$H_3C-(CH_2)_{13}-C(O)-NH-(CH_2)_3N^+$
$(CH_3)_2CH_2COO^-$

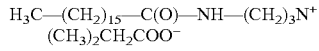
$H_3C-(CH_2)_{15}-C(O)-NH-(CH_2)_3N^+$
$(CH_3)_2CH_2COO^-$

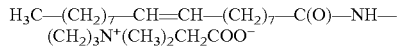
$H_3C-(CH_2)_7-CH=CH-(CH_2)_7-C(O)-NH-$
$(CH_2)_3N^+(CH_3)_2CH_2COO^-$ Particularly preferably, surfactants of the formula (Bet-I) are used within relatively narrow quantitative ranges. In this case, agents according to the invention are preferred which include—based on their weight—0.25 to 8 wt. %, more preferably 0.5 to 7 wt. %, more preferably 0.75 to 6.5 wt. % and in particular 1 to 5.5 wt. % surfactant(s) of the formula (Bet-I).

In addition to or instead of the amphosurfactant(s) of the formula (Bet-I), the hair treatment agents according to the invention can, with particular preference, include as amphoteric surfactants betaines of the formula (Bet-II)

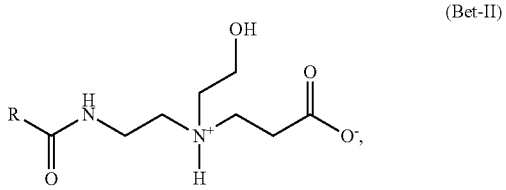

(Bet-II)

in which R denotes a straight-chained or branched, saturated or mono- or polyunsaturated alkyl or alkenyl residue with 8 to 24 carbon atoms.

These surfactants are referred to according to INCI nomenclature as Amphoacetates, the representatives derived from coconut fatty acids being preferred and being referred to as Cocoamphoacetates.

For technical reasons related to manufacturing, surfactants of this type always also include betaines of the formula (Bet-11a)

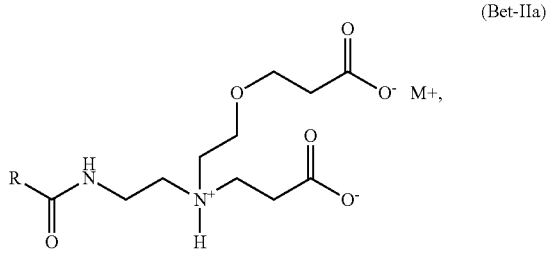

(Bet-IIa)

in which R denotes a straight-chained or branched, saturated or mono- or polyunsaturated alkyl or alkenyl residue with 8 to 24 carbon atoms and M denotes a cation.

These surfactants are referred to according to INCI nomenclature as Amphodiacetates, the representatives derived from coconut fatty acids being preferred and being referred to as Cocoamphodiacetates.

Particularly preferably according to the invention, surfactants of the formula (Bet-II) are used which are a mixture of the following representatives:

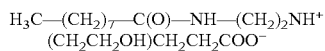
$H_3C-(CH_2)_7-C(O)-NH-(CH_2)_2NH^+$
$(CH_2CH_2OH)CH_2CH_2COO^-$

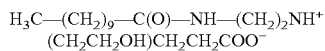
$H_3C-(CH_2)_9-C(O)-NH-(CH_2)_2NH^+$
$(CH_2CH_2OH)CH_2CH_2COO^-$

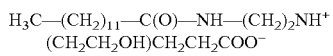
$H_3C-(CH_2)_{11}-C(O)-NH-(CH_2)_2NH^+$
$(CH_2CH_2OH)CH_2CH_2COO^-$

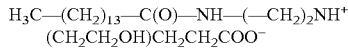
$H_3C-(CH_2)_{13}-C(O)-NH-(-CH_2)_2NH^+$
$(CH_2CH_2OH)CH_2CH_2COO^-$

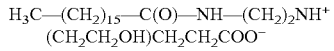
$H_3C-(CH_2)_{15}-C(O)-NH-(CH_2)_2NH^+$
$(CH_2CH_2OH)CH_2CH_2COO^-$

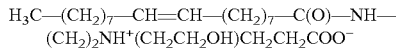
$H_3C-(CH_2)_7-CH=CH-(CH_2)_7-C(O)-NH-$
$(CH_2)_2NH^+(CH_2CH_2OH)CH_2CH_2COO^-$ Particularly preferably, surfactants of the formula (Bet-II) are used within relatively narrow quantitative ranges. In this case, agents according to the invention are preferred which include—based on their weight—0.25 to 8 wt. %, more preferably 0.5 to 7 wt. %, more preferably 0.75 to 6.5 wt. % and in particular 1 to 5.5 wt. % surfactant(s) of the formula (Bet-11).

In summary, hair treatment agents according to the invention are preferred in which the residue R in the formulae (Bet-I) and (Bet-II) is selected from $H_3C-(CH_2)_7-$, $H_3C-(CH_2)_9-$, $H_3C-(CH_2)_{11}-$, $H_3C-(CH_2)_{13}-$, $H_3C-(CH_2)_{15}-$, $H_3C-(CH_2)_7-CH=CH-(CH_2)_7-$ or mixtures thereof.

Particularly preferred nonionic surfactants are alkyl polyglycosides. Accordingly, hair treatment agents according to the invention are preferred which include as nonionic surfactants—based on their weight—0.1 to 20 wt. % alkyl polyglycosides of the general formula $RO-(Z)_x$, wherein R denotes alkyl, Z denotes sugar and x denotes the number of sugar units.

Preferred according to the invention are alkyl polyglycosides corresponding to the general formula $RO-(Z)_x$, wherein R denotes alkyl, Z denotes sugar and x denotes the number of sugar units.

Particularly preferred are those alkyl polyglycosides in which R consists
  substantially of $C_8$- and $C_{10}$-alkyl groups,
  substantially of $C_{12}$- and $C_{14}$-alkyl groups,
  substantially of $C_8$- to $C_{16}$-alkyl groups or
  substantially of $C_{12}$- to $C_{16}$-alkyl groups or
  substantially of $C_{16}$ to $C_{18}$-alkyl groups.

As sugar building block Z, it is possible to use any mono- or oligosaccharides. Sugars with 5 or 6 carbon atoms and the corresponding oligosaccharides are generally used. Sugars of this type are for example glucose, fructose, galactose, arabinose, ribose, xylose, lyxose, allose, altrose, mannose, gulose, idose, talose and sucrose. Preferred sugar building blocks are glucose, fructose, galactose, arabinose and sucrose; glucose is particularly preferred.

The alkyl polyglycosides that can be used according to the invention include on average 1.1 to 5 sugar units. Alkyl polyglycosides with x values of 1.1 to 2.0 are preferred. Most particularly preferred are alkyl glycosides in which x is 1.1 to 1.8.

Other surfactants which can be used particularly advantageously in the agents according to the invention—particularly in a mixture with alkyl polyglycosides—are glutamates, aspartates and sulfoacetates. In this case, hair treatment agents according to the invention are preferred which include—based on their weight—0.1 to 20 wt. % fatty acid glutamates (acylglutamates) and/or fatty acid aspartates (acyl aspartates) and/or alkyl sulfoacetates (sulfoacetic acid alkyl esters).

Acylglutamates can be described by the formula

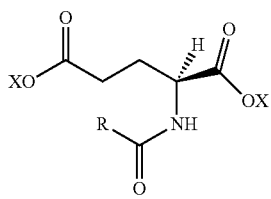

in which R—CO denotes a linear or branched acyl residue with 6 to 22 carbon atoms and 0 and/or 1, 2 or 3 double bonds and X denotes hydrogen, an alkali metal and/or alkaline earth metal, ammonium, alkylammonium, alkanolammonium or glucammonium. Surprisingly, it has been found that mixtures of alkyl glucosides with acylglutamates exhibit very good dermatological compatibility and an improved foaming power with respect to both base foam and foam stability in the presence of water hardness.

Acylglutamates represent known anionic surfactants which can be obtained for example by Schotten-Baumann acylation of glutamic acid with fatty acids, fatty acid esters or fatty acid chlorides. Commercial products are available for example from Hoechst AG, Frankfurt/DE or Ajinomoto Co. Inc., Tokyo/JP.

Typical examples of suitable acylglutamates are anionic surfactants derived from fatty acids with 6 to 22, preferably 12 to 18 carbon atoms, such as e.g. C12/14 or C12/18 coconut fatty acid, lauric acid, myristic acid, palmitic acid and/or stearic acid. Particularly preferred are sodium N-cocoyl and sodium N-stearoyl L-glutamate.

The agents according to the invention can include the alkyl and/or alkenyl oligoglucosides and the acylglutamates in a weight ratio of 1:99 to 99:1, preferably 10:90 to 90:10 and in particular 80:20 to 50:50.

Acyl aspartates can be described by the formula

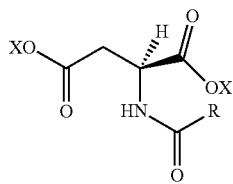

in which R—CO denotes a linear or branched acyl residue with 6 to 22 carbon atoms and 0 and/or 1, 2 or 3 double bonds and X denotes hydrogen, an alkali metal and/or alkaline earth metal, ammonium, alkylammonium, alkanolammonium or glucammonium.

Acyl aspartates represent known anionic surfactants which can be obtained for example by Schotten-Baumann acylation of aspartic acid with fatty acids, fatty acid esters or chlorides. Commercial products are available for example from Hoechst AG, Frankfurt/DE or Ajinomoto Co. Inc., Tokyo/JP.

Typical examples of suitable acyl aspartates are anionic surfactants derived from fatty acids with 6 to 22, preferably 12 to 18 carbon atoms, such as for example C12/14- or C12/18-coconut fatty acid, lauric acid, myristic acid, palmitic acid and/or stearic acid. Particularly preferred are sodium N-cocoyl and sodium N-stearoyl L-aspartate.

The agents according to the invention can likewise include the alkyl and/or alkenyl oligoglucosides and the acyl aspartates in a weight ratio of 1:99 to 99:1, preferably 10:90 to 90:10 and in particular 80:20 to 50:50.

Sulfoacetates (sulfoacetic acid esters) are generally salts of esters of sulfoacetic acid and can be described by the general formula $$R—O—C(O)—CH_2—SO_2—OX$$

in which R denotes a linear or branched alkyl or alkenyl residue with 6 to 22 carbon atoms and 0 and/or 1, 2 or 3 double bonds and X denotes hydrogen, an alkali metal and/or alkaline earth metal, ammonium, alkylammonium, alkanolammonium or glucammonium.

Particularly preferred is the use of the sodium salt of sulfoacetic acid with the INCI name: Sodium Lauryl Sulfoacetate):

$$H_3C—(CH_2)_{11}—O—CO—CH_2—SO_2—ONa.$$

Sodium Lauryl Sulfoacetate is a white, free-flowing powder, which gives a neutral reaction, having good foaming power, wetting power and dispersing power.

Cationic surfactants of the type of the quaternary ammonium compounds, ester quats and amidoamines can be used according to the invention. Preferred quaternary ammonium compounds are ammonium halides, in particular chlorides and bromides, such as alkyltrimethylammonium chlorides, dialkyldimethylammonium chlorides and trialkylmethylammonium chlorides. The long alkyl chains of these surfactants preferably have 10 to 18 carbon atoms, such as e.g. in cetyltrimethylammonium chloride, stearyl-trimethylammonium chloride, distearyldimethylammonium chloride, lauryldimethylammonium chloride, lauryldimethylbenzylammonium chloride and tricetylmethylammonium chloride. Other preferred cationic surfactants are the imidazolium compounds known by the INCI names Quaternium-27 and Quaternium-83.

Particularly preferred hair cleansers according to the invention are characterized in that they include as cationic care substance—based on their weight—0.05 to 7.5 wt. %, preferably 0.1 to 5 wt. %, particularly preferably 0.2 to 3.5 wt. % and in particular 0.25 to 2.5 wt. % cationic surfactant(s) from the group of the quaternary ammonium compounds and/or esterquats and/or amidoamines, wherein preferred cationic surfactant(s) is/are selected from alkyltrimethylammonium chlorides with preferably 10 to 18 carbon atoms in the alkyl residue and/or dialkyldimethylammonium chlorides with preferably 10 to 18 carbon atoms in the alkyl residue and/or trialkylmethylammonium chlorides with preferably 10 to 18 carbon atoms in the alkyl residue and/or cetyltrimethylammonium chloride and/or stearyltrimethylammonium chloride and/or distearyldimethylammonium chloride and/or lauryldimethyl ammonium chloride and/or lauryldimethylbenzylammonium chloride and/or tricetylmethylammonium chloride and/or Quaternium-27 and/or Quaternium-83 and/or N-methyl-N-(2-hydroxyethyl)-N,N-(ditallow acyloxyethyl) ammonium methosulfate and/or N-methyl-N-(2-hydroxyethyl)-N,N-(distearoyloxyethyeammonium methosulfate and/or N,N-dimethyl-N,N-distearoyloxyethylammonium chloride and/or N,N-di-(2-hydroxyethyl)-N,N-(fatty acid ester ethyl)ammonium chloride.

The care effects of the agents according to the invention can be enhanced still further by using specific care substances. These are preferably selected from specific groups of care substances that are known per se, since these care substances harmonize extremely well with the 4-morpholinomethyl-substituted silicones used according to the invention with respect to formulating technology and the care effect.

Preferred hair treatment agents according to the invention are characterized in that they additionally include care substance(s)—based on their weight—in quantities of 0.001 to 10 wt. %, preferably 0.005 to 7.5 wt. %, particularly preferably 0.01 to 5 wt. % and in particular 0.05 to 2.5 wt. %, preferred care substance(s) being selected from the group of i. L-carnitine and/or salts thereof;
  ii. panthenol and/or pantothenic acid;
  iii. the 2-furanones and/or derivatives thereof, in particular pantolactone;
  iv. taurine and/or salts thereof;
  v. niacinamide;
  vi. ubiquinone;
  vii. ectoine;
  viii. allantoin.

In this embodiment of hair treatment agents according to the invention, the 4-morpholinomethyl-substituted silicones are combined with at least one care substance, which is selected from L-carnitine and/or salts thereof, panthenol and/or pantothenic acid, 2-furanones and/or derivatives thereof, in particular pantolactone, taurine and/or salts thereof, niacinamide, ubiquinones, ectoine, allantoin. These care substances are described below.

L-Carnitine (IUPAC name (R)-(3-carboxy-2-hydroxypropyl)-N,N,N-trimethylammonium hydroxide) is a naturally occurring, vitamin-like substance. As a betaine, L-carnitine can form addition compounds and double salts. Preferred L-carnitine derivatives according to the invention are selected in particular from acetyl L-carnitine, L-carnitine fumarate, L-carnitine citrate, lauroyl L-carnitine and particularly preferably L-carnitine tartrate. The aforementioned L-carnitine compounds are available e.g. from Lonza GmbH (Wuppertal, Germany).

Preferred hair treatment agents according to the invention are characterized in that they include—based on their weight—0.001 to 10 wt. %, preferably 0.005 to 7.5 wt. %, particularly preferably 0.01 to 5 wt % and in particular 0.05 to 2.5 wt. % L-carnitine or L-carnitine derivatives, preferred L-carnitine derivatives being selected from acetyl L-carnitine, L-carnitine fumarate, L-carnitine citrate, lauroyl L-carnitine and in particular L-carnitine tartrate.

Panthenol (IUPAC name: (+)-(R)-2,4-dihydroxy-N-(3-hydroxypropyl)-3,3-dimethylbutyramide) is converted to pantothenic acid in the body. Pantothenic acid is a vitamin from the B vitamin group (vitamin B5).

Preferred hair treatment agents according to the invention are characterized in that they include—based on its weight—0.01 to 5 wt. %, preferably 0.05 to 2.5 wt. %, particularly preferably 0.1 to 1.5 wt. % and in particular 0.25 to 1 wt. % panthenol ((±)-2,4-dihydroxy-N-(3-hydroxypropyl)-3,3-dimethylbutyramide).

Preferred hair treatment agents according to the invention include—based on their weight—0.01 to 15 wt. %, preferably 0.025 to 12.5 wt. %, particularly preferably 0.05 to 10 wt. %, more preferably 0.1 to 7.5 wt. % and in particular 0.5 to 5 wt. % of at least one 2-furanone derivative of the formula (Fur-I) and/or of the formula (Fur-II)

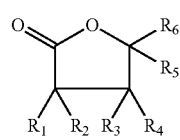
(Fur-I)

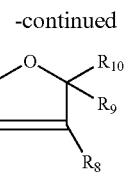
(Fur-II)

in which the residues $R^1$ to $R^{10}$ independently of one another denote:

hydrogen, —OH, a methyl, methoxy, aminomethyl or hydroxymethyl residue,
—$C_2$-$C_4$-saturated or mono- or diunsaturated, branched or linear hydrocarbon residue,
—$C_2$-$C_4$-saturated or mono- or diunsaturated, branched or linear mono-, di- or trihydroxy hydrocarbon residue,
—$C_2$-$C_4$-saturated or mono- or diunsaturated, branched or linear mono-, di- or triamino hydrocarbon residue,
a group —$OR^{11}$, with $R^{11}$ as a —$C_2$-$C_4$-saturated or mono- or diunsaturated, branched or linear hydrocarbon residue, —$C_2$-$C_4$-saturated or mono- or diunsaturated, branched or linear mono-, di- or trihydroxy hydrocarbon residue,
a group —$NR^{12}R^{13}$, wherein $R^{12}$ and $R^{13}$ each independently of one another denote hydrogen, a methyl, a —$C_2$-$C_4$-saturated or mono- or diunsaturated, branched or linear hydrocarbon residue, a —$C_2$-$C_4$-saturated or mono- or diunsaturated, branched or linear mono-, di- or trihydroxy hydrocarbon residue,
a group —$COOR^{14}$, wherein $R^{14}$ denotes hydrogen, a methyl, a —$C_2$-$C_4$-saturated or mono- or diunsaturated, branched or linear hydrocarbon residue, a —$C_2$-$C_4$-saturated mono- or diunsaturated, branched or linear mono-, di- or trihydroxy hydrocarbon residue, a —$C_2$-$C_4$-saturated or mono- or diunsaturated, branched or linear mono-, di- or triamino hydrocarbon residue,
a group —$CONR^{15}R^{16}$, wherein $R^{15}$ and $R^{16}$ each denote hydrogen, methyl, a —$C_2$-$C_4$-saturated or mono- or diunsaturated, branched or linear hydrocarbon residue, a —$C_2$-$C_4$-saturated mono- or diunsaturated, branched or linear mono-, di- or trihydroxy hydrocarbon residue, a —$C_2$-$C_4$-saturated or mono- or diunsaturated, branched or linear mono-, di- or triamino hydrocarbon residue,
a group —$COR^{16}$, wherein $R^{16}$ denotes a methyl, a —$C_2$-$C_4$-saturated or mono- or diunsaturated, branched or linear hydrocarbon residue, a —$C_2$-$C_4$-saturated or mono- or diunsaturated, branched or linear mono-, di- or trihydroxy hydrocarbon residue, a —$C_2$-$C_4$-saturated or mono- or diunsaturated, branched or linear mono-, di- or triamino hydrocarbon residue,
a group —$OCOR^{17}$, wherein $R^{17}$ denotes a methyl, a —$C_2$-$C_{30}$-saturated or mono- or polyunsaturated, branched or linear hydrocarbon residue, a —$C_2$-$C_{30}$-saturated or mono- or polyunsaturated, branched or linear mono-, di-, tri or polyhydroxy hydrocarbon residue, a —$C_2$-$C_{30}$-saturated or mono- or polyunsaturated, branched or linear mono-, di-, tri or polyamino hydrocarbon residue,
with the proviso that in the event that $R^7$ and $R^8$ denote —OH and at the same time $R^9$ or $R^{10}$ denotes hydrogen, the remaining group $R^9$ or $R^{10}$ does not denote a dihydroxyethyl residue.

Another preferred care substance possessing activating properties that can be used is taurine. Preferred hair treatment agents according to the invention include—based on their weight—0.01 to 15 wt. %, preferably 0.025 to 12.5 wt. %, particularly preferably 0.05 to 10 wt. %, more preferably 0.1 to 7.5 wt. % and in particular 0.5 to 5 wt. % taurine (2-aminoethanesulfonic acid).

Another preferred group of care substances in the agents according to the invention are vitamins, provitamins or vitamin precursors. These are described below:

The group of substances referred to as vitamin A includes retinol (vitamin $A_1$) and 3,4-didehydroretinol (vitamin $A_2$). β-Carotene is the provitamin of retinol. Suitable according to the invention as vitamin A component are e.g. vitamin A acid and esters thereof, vitamin A aldehyde and vitamin A alcohol and esters thereof, such as the palmitate and the acetate. The agents according to the invention include the vitamin A component preferably in quantities of 0.05-1 wt. %, based on the overall preparation.

The vitamin B group or vitamin B complex includes, inter alia:

Vitamin Bi (thiamine)
Vitamin B2 (riboflavin)
Vitamin $B_3$. This name often covers the compounds nicotinic acid and nicotinamide (niacinamide). Preferred according to the invention is nicotinamide, which is included in the agents used according to the invention preferably in quantities of 0.05 to 1 wt. %, based on the overall agent.
Vitamin $B_5$ (pantothenic acid, panthenol and pantolactone). Within the framework of this group, preferably panthenol and/or pantolactone is used (see below). Derivatives of panthenol that can be used according to the invention are in particular the esters and ethers of panthenol and cationically derivatized panthenols. The aforementioned compounds of the vitamin $B_5$ type are included in the agents according to the invention preferably in quantities of 0.05-10 wt. %, based on the overall agent. Quantities of 0.1-5 wt. % are particularly preferred.
Vitamin $B_6$ (pyridoxine as well as pyridoxamine and pyridoxal).
Vitamin C (ascorbic acid). Vitamin C is used in the agents according to the invention preferably in quantities of 0.1 to 3 wt. %, based on the overall agent. Use in the form of the palmitic acid ester, glucosides or phosphates can be preferred. Use in combination with tocopherols can likewise be preferred.
Vitamin E (tocopherols, in particular α-tocopherol). Tocopherol and derivatives thereof, including in particular the esters, such as the acetate, the nicotinate, the phosphate and the succinate, are included in the agents according to the invention preferably in quantities of 0.05-1 wt. %, based on the overall agent.
Vitamin F. The term "vitamin F" is generally understood to mean essential fatty acids, in particular linoleic acid, linolenic acid and arachidonic acid.
Vitamin H. The compound (3aS,4S,6aR)-2-oxohexahydrothieno[3,4-d]-imidazole-4-valeric acid is referred to as vitamin H, but its trivial name biotin has now become accepted. Biotin is included in the agents according to the invention preferably in quantities of 0.0001 to 1.0 wt. %, in particular in quantities of 0.001 to 0.01 wt. %.

In summary, hair treatment agents according to the invention are preferred which include—based on their weight—0.1 to 5 wt. %, preferably 0.2 to 4 wt. %, particularly preferably 0.25 to 3.5 wt. %, more preferably 0.5 to 3 wt. % and in particular 0.5 to 2.5 wt. % vitamins and/or pro-vitamins and/or vitamin precursors, which preferably belong to the groups A, B, C, E, F and H, wherein preferred agents include-2,4-dihydroxy-N-(3-hydroxypropyl)-3,3-dimethylbutyramide, provitamin $B_5$) and/or pantothenic acid (vitamin $B_3$, vitamin $B_5$) and/or niacin, niacinamide or nicotinamide (vitamin $B_3$) and/or L-ascorbic acid (vitamin C) and/or thiamine (vitamin $B_1$) and/or riboflavin (vitamin $B_2$, vitamin G) and/or biotin (vitamin $B_7$, vitamin H) and/or folic acid (vitamin $B_9$, vitamin $B_c$ or vitamin M) and/or vitamin B6 and/or vitamin $B_{12}$.

It has been shown that specific quinones have a particular suitability as a care substance. As an additional care substance, the agents according to the invention can therefore include 0.0001 to 5 wt. % of at least one bioquinone of the formula (Ubi)

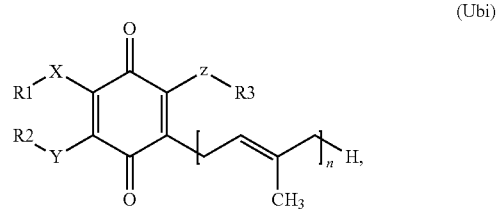

(Ubi)

in which
X, Y, Z independently of one another denote —O— or —NH— or $NR^4$— or a chemical bond
$R^1, R^2, R^3$ independently of one another denote a hydrogen atom or an optionally substituted aryl group or an optionally substituted ($C_1$-$C_6$) alkyl group or a hydroxyalkyl group or a polyhydroxyalkyl group or an optionally substituted ($C_1$-$C_6$) alkylene group or a ($C_1$-$C_6$) acyl residue, wherein preferred residues are selected independently of one another from —H, —$CH_3$, —$CH_2CH_3$, —$(CH_2)_2CH_2$, —$CH(CH_3)_2$, —$(CH_2)_3CH_3$, —$CH(CH_3)CH_2CH_3$, —$CH_2CH(CH_3)_2$, —$C(CH_3)_3$
$R^4$ denotes —$CH_3$, —$CH_2CH_3$, —$(CH_2)_2CH_2$, —$CH(CH_3)_2$, —$(CH_2)_3CH_3$, $CH(CH_3)CH_2CH_3$, —$CH_2CH(CH_3)_2$, —$C(CH_3)_3$
n denotes values of 1 to 20, preferably of 2 to 15 and in particular denotes 5, 6, 7, 8, 9, 10.

Particularly preferred hair treatment agents according to the invention are characterized in that they include as care substance—based on their weight—0.0001 to 1 wt. %, preferably 0.001 to 0.5 wt. % and particularly preferably 0.005 to 0.1 wt. % of at least one ubiquinone and/or of at least one ubiquinol and/or of at least one derivative of these substances, wherein preferred agents include an ubiquinone of the formula (Ubi)

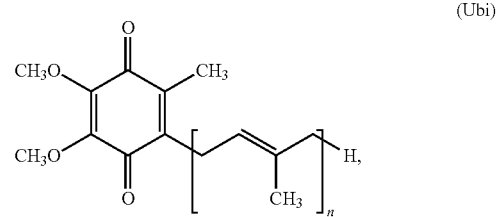

(Ubi)

in which n denotes the values=6, 7, 8, 9 or 10, particularly preferably 10 (coenzyme Q10).

Alternatively to the particularly preferred ubiquinones or in addition thereto, the agents according to the invention can also include plastoquinones. In this case, preferred agents according to the invention are characterized in that they include 0.0002 to 4 wt. %, preferably 0.0005 to 3 wt. %, particularly preferably 0.001 to 2 wt. %, more preferably 0.0015 to 1 and in particular 0.002 to 0.5 wt. % of at least one plastoquinone of the formula (Ubi-b)

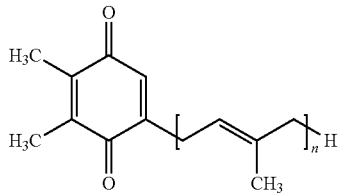

in which n denotes values of 1 to 20, preferably of 2 to 15 and in particular 5, 6, 7, 8, 9, 10, wherein agents particularly preferably include plastoquinone PQ-9 of the formula

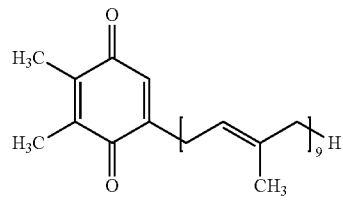

As an additional care enhancer, the agents according to the invention can include ectoine. Ectoine ((4S)-2-methyl-1,4,5,6-tetrahydropyrimidine-4-carboxylic acid) is a natural substance belonging to the group of the compatible solutes. The strongly water-binding low molecular weight organic compound occurs in halophilic bacteria and enables these extremophilic organisms to survive under stress conditions. Preferred hair treatment agents according to the invention are characterized in that they include—based on their weight—0.001 to 10 wt. %, preferably 0.01 to 5 wt. %, particularly preferably 0.05 to 2.5 wt. % and in particular 0.1 to 1 wt. % (S)-2-methyl-1,4,5,6-tetrahydro-4-pyrimidinecarboxylic acid (ectoine) and the physiologically acceptable salts of this compound and/or (S,S)-5-hydroxy-2-methyl-1,4,5,6-tetrahydro-4-pyrimidinecarboxylic acid (hydroxyectoine) and the physiologically acceptable salts of this compound.

Another care substance is allantoin (5-ureidohydantoin, N-(2,5-dioxo-4-imidazolidinyl)urea). Particularly preferred hair treatment agents according to the invention include—based on their weight—0.001 to 10 wt. %, preferably 0.01 to 5 wt. %, particularly preferably 0.05 to 2.5 wt. % and in particular 0.1 to 1 wt. % 5-ureidohydantoin (allantoin).

To improve the elasticity and strengthen the internal structure of hair that has been treated with agents according to the invention, the agents according to the invention can include purine and/or purine derivatives as care substance. In particular the combination of purine and/or purine derivatives with ubiquinones and/or plastoquinones as care substance leads to hair that has been treated with corresponding agents displaying higher measured values in differential thermal analysis and improved wet and dry combability, inter alia.

Purine (7H-imidazo[4,5-d]pyrimidine) does not occur in free form in nature but forms the parent substance of the purines. Purines themselves are a group of important compounds which are widespread in nature and take part in human, animal, plant and microbial metabolic processes and are derived from the parent substance by substitution with OH, $NH_2$, SH in 2-, 6- and 8-position and/or with $CH_3$ in 1-, 3-, 7-position. Purine can be produced for example from aminoacetonitrile and formamide. Purines and purine derivatives are often isolated from natural substances, but can also be produced synthetically by many routes.

Preferred agents according to the invention include purine and/or purine derivatives in relatively narrow quantitative ranges. In this case, preferred cosmetic agents according to the invention are characterized in that they include—based on their weight—0.001 to 2.5 wt. %, preferably 0.0025 to 1 wt. %, particularly preferably 0.005 to 0.5 wt. % and in particular 0.01 to 0.1 wt. % purine(s) and/or purine derivative(s).

Some representatives of purine, the purines and the purine derivatives are particularly preferred according to the invention. Preferred hair treatment agents according to the invention are characterized in that they include as care substance—based on their weight—0.001 to 2.5 wt. %, preferably 0.0025 to 1 wt. %, particularly preferably 0.005 to 0.5 wt. % and in particular 0.01 to 0.1 wt. % purine(s) and/or purine derivative(s), wherein preferred agents include purine and/or purine derivative(s) of the formula (Pur-I)

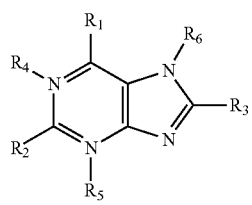

in which the residues $R^1$, $R^2$ and $R^3$, independently of one another, are selected from —H, —OH, $NH_2$, —SH and the residues $R^4$, $R^5$ and $R^6$, independently of one another, are selected from —H, —$CH_3$ and —$CH_2$—$CH_3$, wherein the following compounds are preferred:
purine($R^1$=$R^2$=$R^3$=$R^4$=$R^5$=$R^6$=H)
adenine ($R^1$=$NH_2$, $R^2$=$R^3$=$R^4$=$R^5$=$R^6$=)
guanine ($R^1$=OH, $R^2$=$NH_2$, $R^3$=$R^4$=$R^5$=$R^6$=H)
uric acid ($R^1$=$R^2$=$R^3$=OH, $R^4$=$R^5$=$R^6$=H)
hypoxanthine ($R^1$=OH, $R^2$=$R^3$=$R^4$=$R^5$=$R^6$=H)
6-purinethiol ($R^1$=SH, $R^2$=$R^3$=$R^4$=$R^5$=$R^6$=H)
6-thioguanine ($R^1$=SH, $R^2$=$NH_2$, $R^3$=$R^4$=$R^5$=$R^6$=H)
xanthine ($R^1$=$R^2$=OH, $R^3$=$R^4$=$R^5$=$R^6$=H)
caffeine ($R^1$=$R^2$=OH, $R^3$=H, $R^4$=$R^5$=$R^6$=$CH_3$)
theobromine ($R^1$=$R^2$=OH, $R^3$=$R^4$=H, $R^5$=$R^6$=$CH_3$)
theophylline ($R^1$=$R^2$=OH, $R^3$=H, $R^4$=$CH_3$, $R^5$=$CH_3$, $R^6$=H).

It is furthermore advantageous to use purine or purine derivatives and bioquinones in a specific ratio to one another. In this case, agents according to the invention are preferred in which the weight ratio of purine (derivative(s)) and bioquinone(s) is 10:1 to 1:100, preferably 5:1 to 1:50, particularly preferably 2:1 to 1:20 and in particular 1:1 to 1:10.

As already mentioned, caffeine is a particularly preferred purine derivative and coenzyme Q10 is a particularly preferred bioquinone. Particularly preferred agents according to the invention are therefore characterized in that they include—based on their weight—0.001 to 2.5 wt. %, preferably 0.0025 to 1 wt. %, particularly preferably 0.005 to 0.5 wt. % and in particular 0.01 to 0.1 wt. % caffeine and 0.0002 to 4 wt. %, preferably 0.0005 to 3 wt. %, particularly preferably 0.001 to 2 wt. %, more preferably 0.0015 to 1 and in particular 0.002 to 0.5 wt. % coenzyme Q10.

As care substance, the agents according to the invention can also include flavonoids. The flavonoids are a group of water-soluble plant dyes and play an important part in the metabolism of many plants. Together with the phenolic acids, they belong to the polyphenols. Well in excess of 6500 different flavonoids are known, which can be divided into flavonols, flavones, flavanones, isoflavonoids and anthocyans.

According to the invention, flavonoids from all six groups can be used, with specific representatives of the individual groups being preferred as care substance owing to their particularly intensive action. Preferred flavonols are quercetin, rutin, kaempferol, myricetin, isorhamnetin, preferred flavanols are catechin, gallocatechin, epicatechin, epigallocatechin gallate, theaflavin, thearubigin, preferred flavones are luteolin, apigenin, morin, preferred flavanones are hesperetin, naringenin, eriodictyol, preferred isoflavonoids are genistein, daidzein, and preferred anthocyanidins (anthocyans) are cyanidin, delphinidin, malvidin, pelargonidin, peonidin, petunidin.

Particularly preferred hair treatment agents according to the invention are characterized in that they include—based on their weight—0.001 to 2.5 wt. %, preferably 0.0025 to 1 wt. %, particularly preferably 0.005 to 0.5 wt. % and in particular 0.01 to 0.1 wt. % flavonoids, in particular flavonols, particularly preferably 3,3',4',5,7-pentahydroxyflavone (quercetin) and/or 3,3',4',5,7-pentahydroxyflavone-3-O-rutinoside (rutin).

Also preferred is the use of bisabolol and/or bisabolol oxides as care substance in the agents according to the invention. In this case, hair treatment agents according to the invention are preferred which additionally include 0.001 to 5 wt. %, preferably 0.01 to 4 wt. %, particularly preferably 0.02 to 2.5 wt. % and in particular 0.1 to 1.5 wt. % bisabolol and/or oxides of bisabolol, preferably (−)-alpha-bisabolol.

Creatine is also suitable according to the invention as a care substance. Creatine (3-methylguanidinoacetic acid) is an organic acid, which inter alia contributes to supplying energy to the muscles in vertebrates. Creatine is synthesized in the kidney, liver and pancreas. It is formally derived from the amino acids glycine and arginine and 95% of it is located in skeletal muscle. Particularly preferred hair treatment agents according to the invention include—based on their weight—0.01 to 15 wt. %, preferably 0.025 to 12.5 wt. %, particularly preferably 0.05 to 10 wt. %, more preferably 0.1 to 7.5 wt. % and in particular 0.5 to 5 wt. % N-methylguanidinoacetic acid (creatine).

The agents according to the invention can, in addition to the above-mentioned ingredients and optional other ingredients, include other substances which prevent, alleviate or cure hair loss. In particular, a content of hair root-stabilizing active substances is advantageous. These substances are described below:

Propecia (finasteride) is currently the only preparation to have been approved worldwide and for which efficacy and tolerability have been proved in numerous studies. Propecia has the effect that less DHT can be produced from testosterone.

Minoxidil is probably the oldest demonstrably effective hair growth agent with or without supplementary additives. For the treatment of hair loss, it must only be used externally. There are hair lotions including 2% to 5% minoxidil, and also gels with up to 15% minoxidil. The effectiveness increases with the dose, but in hair lotions minoxidil is soluble only in a content of up to 5%. In many countries, hair lotions including up to 2% minoxidil are available without a prescription.

Spironolactone can be applied externally in the form of a hair lotion and in combination with minoxidil to combat hormonal influences on the hair follicles. Spironolactone works as an androgen receptor blocker, in other words binding of DHT to the hair follicles is prevented.

In summary, hair treatment agents according to the invention are preferred which additionally include—based on its weight—0.001 to 5 wt. % hair root-stabilizing substances, in particular minoxidil and/or finasteride and/or ketoconazole.

Through additional anti-dandruff active ingredients (e.g. climbazole, piroctone olamine or zinc pyrithione), the quantity of dandruff-causing fungal yeast is selectively reduced, bacterial flora return to their normal percentage composition and desquamation is reduced to the physiological level. Laboratory tests have shown, however, that the various species representatives of Pityrosporum ovale respond with varying success to the anti-dandruff active ingredients. To combat all causes of dandruff with maximum effectiveness, a combination of anti-dandruff active ingredients is therefore most successful.

In summary, hair treatment agents according to the invention are preferred which additionally include—based on their weight—0.001 to 5 wt. % anti-dandruff active ingredients, in particular piroctone olamine (1-hydroxy-4-methyl-6-(2,4,4-trimethylpentyl)pyridine-2(1H)-one, compound with 2-aminoethanol, 1:1) and/or zinc pyrithione and/or selenium sulfide and/or climbazole and/or salicylic acid or fumaric acid.

In addition to the care substances, the agents according to the invention can include other care substances. Their presence is not absolutely essential to achieve the effects according to the invention, but additional effects, such as a pleasant handle or pleasant application feel, can result from the use of these care substances.

As a further ingredient, the agents according to the invention can, with particular preference, include one or more amino acids Amino acids that can be particularly preferably used according to the invention come from the group of glycine, alanine, valine, leucine, isoleucine, phenylalanine, tyrosine, tryptophan, proline, aspartic acid, glutamic acid, asparagine, glutamine, serine, threonine, cysteine, methionine, lysine, arginine, histidine, β-alanine, 4-aminobutyric acid (GABA), betaine, L-cystine (L-Cyss), L-carnitine, L-citrulline, L-theanine, 3',4'-dihydroxy-L-phenylalanine (L-Dopa), 5'-hydroxy-L-tryptophan, L-homocysteine, S-methyl-L-methionine, S-allyl-L-cysteine sulfoxide (L-alliin), L-trans-4-hydroxyproline, L-5-oxoproline (L-pyroglutamic acid), L-phosphoserine, creatine, 3-methyl-L-histidine and L-ornithine, it being possible to use both the individual amino acids and mixtures.

Preferred agents according to the invention include one or more amino acids in relatively narrow quantitative ranges. In this case, preferred hair treatment agents according to the invention are characterized in that they include as care substance—based on their weight—0.01 to 5 wt. %, preferably 0.02 to 2.5 wt. %, particularly preferably 0.05 to 1.5 wt. %, more preferably 0.075 to 1 wt. % and in particular 0.1 to 0.25 wt. % amino acid(s), preferably from the group of glycine and/or alanine and/or valine and/or lysine and/or leucine and/or threonine.

As a further constituent, the agents according to the invention can include at least one carbohydrate from the group of the monosaccharides, disaccharides and/or oligosaccharides. In this case, preferred hair treatment agents according to the invention are characterized in that they include as care substance—based on their weight—0.01 to 5 wt. %, preferably 0.05 to 4.5 wt. %, particularly preferably 0.1 to 4 wt. %, more preferably 0.5 to 3.5 wt. % and in particular 0.75 to 2.5 wt. % carbohydrate(s), selected from monosaccharides, disaccharides and/or oligosaccharides, wherein preferred carbohydrates are selected from monosaccharides, in particular D-ribose and/or D-xylose and/or L-arabinose and/or D-glucose and/or D-mannose and/or D-galactose and/or D-fructose and/or sorbose and/or L-fucose and/or L-rhamnose as well as disaccharides, in particular sucrose and/or maltose and/or lactose and/or trehalose and/or cellobiose and/or gentiobiose and/or isomaltose.

Particularly preferred agents according to the invention include, based on their weight, 0.005 to 0.015 wt. % caffeine and 0.75 to 1.5 wt. % glucose monohydrate, 0.005 to 0.015 wt. % caffeine and 0.75 to 1.5 wt. % sucrose, 0.005 to 0.015 wt. % caffeine and 0.75 to 1.5 wt. % fructose.

As already mentioned, preferred agents according to the invention include (an) amino acid(s).

Amino acids that can be used particularly preferably according to the invention come from the group of glycine, alanine, valine, leucine, isoleucine, phenylalanine, tyrosine, tryptophan, proline, aspartic acid, glutamic acid, asparagine, glutamine, serine, threonine, cysteine, methionine, lysine, arginine, histidine, β-alanine, 4-aminobutyric acid (GABA), betaine, L-cystine (L-Cyss), L-carnitine, L-citrulline, L-theanine, 3',4'-dihydroxy-L-phenylalanine (L-Dopa), 5'-hydroxy-L-tryptophan, L-homocysteine, S-methyl-L-methionine, S-allyl-L-cysteine sulfoxide (L-alliin), L-trans-4-hydroxyproline, L-5-oxoproline (L-pyroglutamic acid), L-phosphoserine, creatine, 3-methyl-L-histidine, L-ornithine, it being possible to use both the individual amino acids and mixtures.

Preferred agents according to the invention include one or more amino acids in relatively narrow quantitative ranges. In this case, preferred cosmetic agents according to the invention are characterized in that they additionally include—0.05 to 5 wt. %, preferably 0.1 to 2.5 wt. %, particularly preferably 0.15 to 1 wt. % and in particular 0.2 to 0.5 wt. % amino acid(s), preferably (an) amino acid(s) from the group of glycine and/or alanine and/or valine and/or lysine and/or leucine and/or threonine.

Particularly preferred agents according to the invention include, based on their weight, 0.005 to 0.015 wt. % caffeine and 0.75 to 1.5 wt. % glucose monohydrate and 0.1 to 0.25 wt. % glycine, 0.005 to 0.015 wt. % caffeine and 0.75 to 1.5 wt. % sucrose and 0.1 to 0.25 wt. % glycine, 0.005 to 0.015 wt. % caffeine and 0.75 to 1.5 wt. % fructose and 0.1 to 0.25 wt. % glycine, 0.005 to 0.015 wt. % caffeine and 0.75 to 1.5 wt. % glucose monohydrate and 0.1 to 0.25 wt. % alanine, 0.005 to 0.015 wt. % caffeine and 0.75 to 1.5 wt. % sucrose and 0.1 to 0.25 wt. % alanine, 0.005 to 0.015 wt. % caffeine and 0.75 to 1.5 wt. % fructose and 0.1 to 0.25 wt. % alanine, 0.005 to 0.015 wt. % caffeine and 0.75 to 1.5 wt. % glucose monohydrate and 0.1 to 0.25 wt. % valine, 0.005 to 0.015 wt. % caffeine and 0.75 to 1.5 wt. % sucrose and 0.1 to 0.25 wt. % valine, 0.005 to 0.015 wt. % caffeine and 0.75 to 1.5 wt. % fructose and 0.1 to 0.25 wt. % valine.

The 4-morpholinomethyl-substituted silicones used according to the invention can of course be used together with other conventional silicones.

Preferred agents according to the invention are characterized in that they include at least one other silicone, preferably a silicone selected from among:

(i) polyalkylsiloxanes, polyarylsiloxanes, polyalkylarylsiloxanes, which are volatile or non-volatile, straight-chained, branched or cyclic, crosslinked or uncrosslinked;

(ii) polysiloxanes which include in their general structure one or more organo functional groups, are selected from among:
 a) substituted or unsubstituted aminated groups;
 b) (per)fluorinated groups;
 c) thiol groups;
 d) carboxylate groups;
 e) hydroxylated groups;
 f) alkoxylated groups;
 g) acyloxyalkyl groups;
 h) amphoteric groups;
 i) bisulfite groups;
 j) hydroxyacylamino groups;
 k) carboxy groups;
 l) sulfonic acid groups; and
 m) sulfate or thiosulfate groups;

(iii) linear polysiloxane (A)—polyoxyalkylene (B) block copolymers of the type $(A-B)_n$ with n>3;

(iv) graft silicone polymers with a non-silicone-including, organic backbone, which consist of an organic main chain, which is formed from organic monomers including no silicone, on to which at least one polysiloxane macromer has been grafted in the chain and optionally on at least one end of the chain;

(v) graft silicone polymers with a polysiloxane backbone, on to which non-silicone-including organic monomers have been grafted having a polysiloxane main chain on to which at least one organic macromer including no silicone has been grafted in the chain and optionally on at least one end thereof;

or mixtures thereof.

Particularly preferred agents according to the invention include the other silicone(s) preferably in quantities of 0.1 to 10 wt. %, preferably of 0.25 to 7 wt % and in particular of 0.5 to 5 wt. %, based in each case on the overall agent.

Preferred silicones are described below.

Particularly preferred agents according to the invention are characterized in that they include at least one silicone of the formula S1-I $$(CH_3)_3Si-[O-Si(CH_3)_2]_x-O-Si(CH_3)_3 \quad (Si-I),$$

in which x denotes a number from 0 to 100, preferably from 0 to 50, more preferably from 0 to 20 and in particular 0 to 10.

These silicones are known as DIMETHICONES according to the INCI nomenclature. Within the framework of the present invention, as silicones of the formula Si-I, the compounds:

$$(CH_3)_3Si-O-Si(CH_3)_3$$

$$(CH_3)_3Si-O-(CH_3)_2Si-O-Si(CH_3)_3$$

$$(CH_3)_3Si-[O-(CH_3)_2Si]_2-O-Si(CH_3)_3$$

$$(CH_3)_3Si-[O-(CH_3)_2Si]_3-O-Si(CH_3)_3$$

$$(CH_3)_3Si-[O-(CH_3)_2Si]_4-O-Si(CH_3)_3$$

$$(CH_3)_3Si-[O-(CH_3)_2Si]_5-O-Si(CH_3)_3$$

$$(CH_3)_3Si-[O-(CH_3)_2Si]_6-O-Si(CH_3)_3$$

$$(CH_3)_3Si-[O-(CH_3)_2Si]_7-O-Si(CH_3)_3$$

$$(CH_3)_3Si-[O-(CH_3)_2Si]_8-O-Si(CH_3)_3$$

$(CH_3)_3Si—[O—(CH_3)_2Si]_9—O—Si(CH_3)_3$ $(CH_3)_3Si—[O—(CH_3)_2Si]_{10}—O—Si(CH_3)_3$ $(CH_3)_3Si—[O—(CH_3)_2Si]_{11}—O—Si(CH_3)_3$ $(CH_3)_3Si—[O—(CH_3)_2Si]_{12}—O—Si(CH_3)_3$ $(CH_3)_3Si[O—(CH_3)_2Si]_3—O—Si(CH_3)_3$ $(CH_3)_3Si—[O—(CH_3)_2Si]_{14}—O—Si(CH_3)_3$ $(CH_3)_3Si—[O—(CH_3)_2Si]_{15}—O—Si(CH_3)_3$ $(CH_3)_3Si—[O—(CH_3)_2Si]_{16}—O—Si(CH_3)_3$ $(CH_3)_3Si—[O—(CH_3)_2Si]_{17}—O—Si(CH_3)_3$ $(CH_3)_3Si—[O—(CH_3)_2Si]_{18}—O—Si(CH_3)_3$ $(CH_3)_3Si—[O—(CH_3)_2Si]_{19}—O—Si(CH_3)_3$ $(CH_3)_3Si—[O—(CH_3)_2Si]_{20}—O—Si(CH_3)_3$ are preferably used, with $(CH_3)_3Si—O—Si(CH_3)_3$, $(CH_3)_3Si—O—(CH_3)_2Si—O—Si(CH_3)_3$ and/or $(CH3)_3Si—[O—(CH_3)_2Si]_2—O—Si(CH_3)_3$ being particularly preferred.

Mixtures of the above silicones can, of course, also be included in the agents according to the invention.

Preferred silicones that can be used according to the invention have viscosities at 20° C. of 0.2 to 2 $mm^2s^{-1}$, with silicones having viscosities of 0.5 to 1 $mm^2s^{-1}$ being particularly preferred.

Particularly preferred agents according to the invention include one or more amino functional silicones. These silicones can be described e.g. by the formula $$M(R_aQ_bSiO_{(4-a-b)/2})_x(R_cSiO_{(4-c)/2})_yM,$$

wherein R in the above formula is a hydrocarbon or a hydrocarbon residue with 1 to about 6 carbon atoms, Q is a polar residue of the general formula —$R^1HZ$, where $R^1$ is a divalent connecting group which is bound to hydrogen and the residue Z, composed of carbon and hydrogen atoms, carbon, hydrogen and oxygen atoms or carbon, hydrogen and nitrogen atoms, and Z is an organic, amino functional residue including at least one amino functional group; "a" assumes values in the range of about 0 to about 2, "b" assumes values in the range of about 1 to about 3, "a"+"b" is less than or equal to 3, and "c" is a number in the range of about 1 to about 3, and x is a number in the range of 1 to about 2,000, preferably of about 3 to about 50 and most preferably of about 3 to about 25, and y is a number in the range of about 20 to about 10,000, preferably of about 125 to about 10,000 and most preferably of about 150 to about 1,000, and M is a suitable silicone end group, as known in the prior art, preferably trimethylsiloxy. Non-limiting examples of the residues represented by R include alkyl residues, such as methyl, ethyl, propyl, isopropyl, isopropyl, butyl, isobutyl, amyl, isoamyl, hexyl, isohexyl and similar; alkenyl residues, such as vinyl, halovinyl, alkyl vinyl, allyl, haloallyl, alkyl allyl; cycloalkyl residues, such as cyclobutyl, cyclopentyl, cyclohexyl and similar; phenyl residues, benzyl residues, halogen hydrocarbon residues, such as 3-chloropropyl, 4-bromobutyl, 3,3,3-trifluoropropyl, chlorocyclohexyl, bromophenyl, chlorophenyl and similar and also sulfur-including residues, such as mercaptoethyl, mercaptopropyl, mercaptohexyl, mercaptophenyl and similar; R is preferably an alkyl residue including 1 to about 6 carbon atoms, and R is most preferably methyl. Examples of $R^1$ include methylene, ethylene, propylene, hexamethylene, decamethylene, —$CH_2CH(CH_3)CH_2$—, phenylene, naphthylene, —$CH_2CH_2SCH_2CH_2$—, —$CH_2CH_2OCH_2$—, —$OCH_2CH_2$—, —$OCH_2CH_2CH_2$—, —$CH_2CH(CH_3)C(O)OCH_2$—, —$(CH_2)_3CC(O)OCH_2CH_2$—, —$C_6H_4C_6H_4$—, —$C_6H_4CH_2C_6H_4$—; and —$(CH_2)_3C(O)SCH_2CH_2$—.

Z is an organic, amino functional residue including at least one functional amino group. One possible formula for Z is $NH(CH_2)_zNH_2$, where z is 1 or more. Another possible formula for Z is —$NH(CH_2)_z(CH_2)_{zz}NH$, where both z and zz independently are 1 or more, wherein this structure encompasses diamino ring structures, such as piperazinyl. Z is most preferably an —$NHCH_2CH_2NH_2$ residue. Another possible formula for Z is —$N(CH_2)_z(CH_2)_{zz}NX_2$ or —$NX_2$, where each X of $X_2$ is selected independently from the group consisting of hydrogen and alkyl groups with 1 to 12 carbon atoms, and zz is 0.

Q is most preferably a polar, amine functional residue of the formula —$CH_2CH_2CH_2NHCH_2CH_2NH_2$. In the formulae, "a" assumes values in the range of about 0 to about 2, "b" assumes values in the range of about 2 to about 3, "a"+"b" is less than or equal to 3 and "c" is a number in the range of about 1 to about 3. The molar ratio of $R_aQ_b SiO_{(4-a-b)/2}$ units to $R_cSiO_{(4-c)/2}$ units is in the range of about 1:2 to 1:65, preferably of about 1:5 to about 1:65 and most preferably of about 1:15 to about 1:20. If one or more silicones of the above formula are used, then the different variable substituents in the above formula can be different in the different silicone components that are present in the silicone mixture.

Preferred agents according to the invention are characterized in that they include an amino functional silicone of the formula (Si-II)

$$R'_aG_{3-a}\text{-}Si(OSiG_2)_n\text{-}(OSiG_bR'_{2-b})_m\text{—}O\text{—}SiG_{3-a}R'_a \quad \text{(Si-II)},$$

where the following meanings apply:

G is —H, a phenyl group, —OH, —O—$CH_3$, —$CH_3$, —O—$CH_2CH_3$, —$CH_2CH_3$, —O—$CH_2CH_2CH_3$, —$CH_2CH_2CH_3$, —O—$CH(CH_3)_2$, —$CH(CH_3)_2$, —O—$CH_2CH_2CH_2CH_3$, —$CH_2CH_2CH_2CH_3$, —O—$CH_2CH(CH_3)_2$, —$CH_2CH(CH_3)_2$, —O—$CH(CH_3)CH_2CH_3$, —$CH(CH_3)CH_2CH_3$, —O—$C(CH_3)_3$, —$C(CH_3)_3$;

a denotes a number between 0 and 3, in particular 0;

b denotes a number between 0 and 1, in particular 1, m and n are numbers, the sum of which (m+n) is between 1 and 2000, preferably between 50 and 150, wherein n preferably assumes values of 0 to 1999 and in particular of 49 to 149 and m preferably assumes values of 1 to 2000, in particular of 1 to 10, R' is a monovalent residue selected from
-Q-N(R")—$CH_2$—$CH_2$—N(R")$_2$
-Q-N(R")$_2$
-Q-N$^+$(R")$_3$A$^-$
-Q-N$^+$H(R")$_2$A$^-$
-Q-N$^+$H$_2$(R")A$^-$
-Q-N(R")—$CH_2$—$CH_2$—N$^+$R"H$_2$A$^-$, wherein each Q denotes a chemical bond, —$CH_2$—, —$CH_2$—$CH_2$—, —$CH_2CH_2CH_2$—, —$C(CH_3)_2$—, —$CH_2CH_2CH_2CH_2$—, —$CH_2C(CH_3)_2$—, —$CH(CH_3)CH_2CH_2$—, R" denotes identical or different residues from the group —H, -phenyl, -benzyl, —$CH_2$—$CH(CH_3)Ph$, the $C_{1-20}$ alkyl residues, preferably —$CH_3$, —$CH_2CH_3$, —$CH_2CH_2CH_3$, —$CH(CH_3)_2$, —$CH_2CH_2CH_2H_3$, —$CH_2CH(CH_3)_2$, —$CH(CH_3)CH_2CH_3$, —$C(CH_3)_3$, and A represents an anion, which is preferably selected from chloride, bromide, iodide or methosulfate.

Particularly preferred agents according to the invention are characterized in that they include at least one amino functional silicone of the formula (Si-IIa)

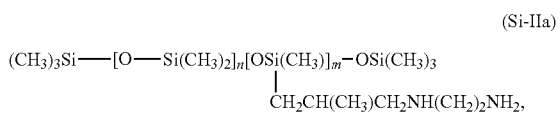
(Si-IIa)

where m and n are numbers, the sum of which (m+n) is between 1 and 2000, preferably between 50 and 150, wherein n preferably assumes values of 0 to 1999 and in particular of 49 to 149 and m preferably assumes values of 1 to 2000, in particular of 1 to 10.

These silicones are known as Trimethylsilylamodimethicones according to the INCI Declaration. Also particularly preferred are agents according to the invention including an amino functional silicone of the formula (Si-IIb)

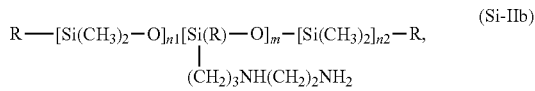
(Si-IIb)

where R denotes —OH, —O—CH$_3$ or a —CH$_3$ group and m, n1 and n2 are numbers, the sum of which (m+n1+n2) is between 1 and 2000, preferably between 50 and 150, wherein the sum (n1+n2) preferably assumes values of 0 to 1999 and in particular of 49 to 149 and m preferably assumes values of 1 to 2000, in particular of 1 to 10.

These silicones are known as Amodimethicones according to the INCI Declaration.

Irrespective of which amino functional silicones are used, agents according to the invention are preferred which include an amino functional silicone of which the amine value is above 0.25 meq/g, preferably above 0.3 meq/g and in particular above 0.4 meq/g. The amine value here denotes the milliequivalents of amine per gram of the amino functional silicone. It can be determined by titration and can also be expressed in the unit mg KOH/g.

Preferred agents according to the invention are characterized in that they include, based on their weight, 0.01 to 10 wt. %, preferably 0.1 to 8 wt. %, particularly preferably 0.25 to 7.5 wt. % and in particular 0.5 to 5 wt. % amino functional silicone(s).

The cyclic dimethicones known according to INCI as CYCLOMETHICONES can also be used with preference according to the invention. In this case, agents according to the invention are preferred which include at least one silicone of the formula Si-III

(Si-III)

in which x denotes a number from 3 to 200, preferably from 3 to 10, more preferably from 30 to 7 and in particular 3, 4, 5 or 6.

The silicones described above have a backbone, which is made up of —Si—O—Si—units. These Si—O—Si—units can also, of course, be interrupted by carbon chains. Corresponding molecules are obtainable via chain-extending reactions and are preferably used in the form of silicone-in-water emulsions.

Agents that are likewise preferred according to the invention are characterized in that they include at least one silicone of the formula Si-IV

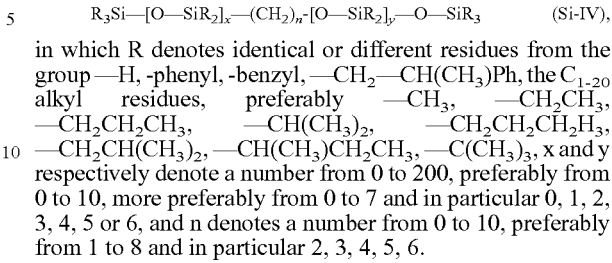

in which R denotes identical or different residues from the group —H, -phenyl, -benzyl, —CH$_2$—CH(CH$_3$)Ph, the C$_{1-20}$ alkyl residues, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, x and y respectively denote a number from 0 to 200, preferably from 0 to 10, more preferably from 0 to 7 and in particular 0, 1, 2, 3, 4, 5 or 6, and n denotes a number from 0 to 10, preferably from 1 to 8 and in particular 2, 3, 4, 5, 6.

The silicones are preferably water-soluble. Preferred agents according to the invention are characterized in that they include at least one water-soluble silicone.

As a further ingredient, the agents according to the invention can include at least one proteolipid of the formula (P-1)

(P-1), in which
R' denotes a straight-chained or branched, saturated or unsaturated hydrocarbon residue with 11 to 24 carbon atoms,
R" signifies a protein, a peptide or a protein hydrolyzate,
X denotes —C(O)O— or —N$^+$(R$^{III}_2$)R$^{IV}$— or —N(R$^{III}$)R$^{IV}$— or —C(O)—N(R$^V$)R$^{VI}$—,
R$^{III}$ signifies —(CH$_2$)$_x$—CH$_3$ with x=0-22 and
R$^{IV}$ signifies —CH$_2$—CH(OH)—CH$_2$— or —(CH$_2$)$_x$— with x=0-22;
R$^V$ and R$^V$ independently of one another denote —H or —(CH$_2$)$_x$—CH$_3$ with x=0-22;
with the proviso that R" denotes keratin or a keratin hydrolyzate if X denotes —C(O)O—.

The proteolipids are preferably used within specific quantities in the agents according to the invention. Preferred hair treatment agents according to the invention include—based on their weight—0.01 to 10 wt. %, preferably 0.02 to 5 wt. %, particularly preferably 0.05 to 2.5 wt. %, more preferably 0.1 to 1 wt. % and in particular 0.15 to 0.5 wt. % proteolipid(s).

The residue R" in formula (P-1) denotes a peptide or a protein or a protein hydrolyzate. If X=—C(O)O—, R" is selected from the group keratin or keratin hydrolyzate.

Preferred residues R" are oligopeptides having at least one amino acid sequence Glu-Glu-Glu, wherein the amino group can be present in free or protonated form and the carboxy groups in free or deprotonated form.

In this and in all of the formulae below, the bracketed hydrogen atom of the amino group as well as the bracketed hydroxy group of the acid function mean that the groups in question can be present as such (in which case it is an oligopeptide with the respective number of amino acids as shown (in the above formula 3) or that the amino acid sequence is present in an oligopeptide which encompasses still further amino acids; depending on where the further amino acid(s) is/are bound, the bracketed components in the above-mentioned formula are replaced by the further amino acid residue(s).

Oligopeptides within the meaning of the present application are condensation products of amino acids linked by amide-type peptide bonds, which encompass at least 3 and a maximum of 25 amino acids.

In preferred hair treatment agents according to the invention of the embodiment described above, the oligopeptide (=the residue R") encompasses 5 to 15 amino acids, preferably 6 to 13 amino acids, particularly preferably 7 to 12 amino acids and in particular 8, 9 or 10 amino acids.

Depending on whether further amino acids are bound to the Glu-Glu-Glu sequence, and depending on the nature of these amino acids, and as a function of the selection of the residues R' and optionally $R^{III}$ and $R^{IV}$, the molar mass of the proteolipid included in the agents according to the invention can vary. Preferred hair treatment agents according to the invention are characterized in that the proteolipid has a molar mass of 1000 to 30000 Da, preferably of 1250 to 25000 Da, particularly preferably of 1500 to 20000 Da and in particular of 2000 to 15000 Da.

As residue R", oligopeptides are preferably used which consist not only of the three glutamic acids but comprise further amino acids bound to this sequence. These further amino acids are preferably selected from specific amino acids, while specific other representatives are less preferred according to the invention.

For instance, it is preferred if the residue R" of the proteolipids used in the agents according to the invention includes no methionine. It is further preferred if the residue R" of the proteolipids used in the agents according to the invention includes no cysteine and/or cystine.

It is further preferred if the residue R" of the proteolipids used in the agents according to the invention includes no aspartic acid and/or asparagine. It is further preferred if the residue R" of the proteolipids used in the agents according to the invention includes no serine and/or threonine.

On the other hand, it is preferred if the residue R" of the proteolipids used in the agents according to the invention includes tyrosine. It is further preferred if the residue R" of the proteolipids used in the agents according to the invention includes leucine. It is further preferred if the residue R" of the proteolipids used in the agents according to the invention includes isoleucine. It is also preferred if the residue R" of the proteolipids used in the agents according to the invention includes arginine. It is further preferred if the residue R" of the proteolipids used in the agents according to the invention includes valine.

Particularly preferred oligopeptides as residue R" or amino acid sequences included in the preferred oligopeptides are described below:

A particularly preferred oligopeptide additionally includes tyrosine, which is preferably bound to the Glu-Glu-Glu sequence via its acid function. Preferred hair treatment agents according to the invention are therefore characterized in that the oligopeptide included in the proteolipids of formula (I) as residue R" has at least one amino acid sequence Tyr-Glu-Glu-Glu, wherein the amino group can be present in free or protonated form and the carboxy groups in free or deprotonated form.

Another particularly preferred oligopeptide additionally includes isoleucine, which is preferably bound to the Glu-Glu-Glu sequence via its amino function. Preferred hair treatment agents according to the invention are therefore characterized in that the oligopeptide included in the proteolipids of formula (I) as residue R" has at least one amino acid sequence Glu-Glu-Glu-Ile, wherein the amino group can be present in free or protonated form and the carboxy groups in free or deprotonated form.

Oligopeptides having both of the above-mentioned amino acids (tyrosine and isoleucine) are preferred according to the invention. Particularly preferred here are hair treatment agents according to the invention in which the oligopeptide included in the proteolipids of formula (I) as residue R" has at least one amino acid sequence Tyr-Glu-Glu-Glu-Ile, wherein the amino group can be present in free or protonated form and the carboxy groups in free or deprotonated form.

Further preferred oligopeptides additionally include arginine, which is preferably present bound to isoleucine. Preferred hair treatment agents according to the invention are therefore characterized in that the oligopeptide included in the proteolipids of formula (I) as residue R" has at least one amino acid sequence Tyr-Glu-Glu-Glu-11e-Arg, wherein the amino groups can be present in free or protonated form and the carboxy groups in free or deprotonated form.

Still further preferred oligopeptides additionally include valine, which is preferably present bound to the arginine. Further preferred hair treatment agents according to the invention are therefore characterized in that the oligopeptide included in the proteolipids of formula (I) as residue R" has at least one amino acid sequence Tyr-Glu-Glu-Glu-Ile-Arg-Val, wherein the amino groups can be present in free or protonated form and the carboxy groups in free or deprotonated form.

Still further preferred oligopeptides additionally include leucine, which is preferably present bound to valine. Further preferred hair treatment agents according to the invention are characterized in that the oligopeptide included in the proteolipids of formula (I) as residue R" has at least one amino acid sequence Tyr-Glu-Glu-Glu-Ile-Arg-Val-Leu, wherein the amino groups can be present in free or protonated form and the carboxy groups in free or deprotonated form.

Particularly preferred oligopeptides additionally include leucine, which is preferably present bound to the tyrosine. Further preferred hair treatment agents according to the invention are characterized in that the oligopeptide included in the proteolipids of formula (I) as residue R" has at least one amino acid sequence Leu-Tyr-Glu-Glu-Glu-Ile-Arg-Val-Leu, wherein the amino groups can be present in free or protonated form and the carboxy groups in free or deprotonated form.

In summary, hair treatment agents according to the invention are particularly preferred which include at least one proteolipid of formula (I), in which R" has at least one amino acid sequence Leu-Tyr-Glu-Glu-Glu-Ile-Arg-Val-Leu, wherein the amino groups can be present in free or protonated form and the carboxy groups in free or deprotonated form.

As already mentioned, R" is selected from the group keratin or keratin hydrolyzate if X=—C(O)O— applies.

In all other cases, the residue R" in formula (P-1) can denote a peptide or a protein or a protein hydrolyzate, with protein hydrolyzates being preferred. Protein hydrolyzates are product mixtures that are obtained by acid-, base- or enzyme-catalyzed degradation of proteins. According to the invention, protein hydrolyzates of both plant and animal origin can be used.

Animal protein hydrolyzates are e.g. elastin, collagen, keratin, silk and/or milk protein hydrolyzates, which can also be present in the form of salts. Products of this type are marketed e.g. with the trade marks Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex) and Kerasol® (Croda).

Preferred according to the invention is the use of protein hydrolyzates of plant origin, e.g. soybean, almond, rice, pea, potato and wheat protein hydrolyzates. Products of this type are available e.g. with the trade marks Gluadin® (Cognis), DiaMin® (Diamalt), Lexein® (Inolex) and Crotein® (Croda).

Preferably, independently of the selection of the X in the formula (P-1), the residue R" is selected from keratin or keratin hydrolyzates. Preferred hair treatment agents according to the invention are characterized in that they include at least one proteolipid of the formula (P-1), in which R" denotes keratin or a keratin hydrolyzate.

In particular, hair treatment agents according to the invention are preferred which include at least one proteolipid of the formula (P-1), in which $R^{III}$ signifies —CH$_3$ and $R^{IV}$ denotes —(CH$_2$)$_x$— with x=0, 1, 2, 3, 4, 5, 6, 7, 8.

Further, particularly preferred hair treatment agents according to the invention are characterized in that they include at least one proteolipid of formula (I), in which X denotes —N$^+$(CH$_3$)$_2$—CH$_2$—CH(OH)—CH$_2$— and R' denotes —(CH$_2$)$_{17}$—CH$_3$.

Likewise further preferred hair treatment agents according to the invention are characterized in that they include at least one proteolipid of the formula (P-1), in which X denotes —C(O)—O— and R' denotes —(CH$_2$)$_{17}$—CH$_3$.

It has proved advantageous to use protein hydrolyzates in addition to the proteolipids. These enhance the action of the proteolipids and are in turn enhanced in their effects. The protein hydrolyzates were described in detail above as residue R". In summary, hair treatment agents according to the invention are preferred which additionally include—based on their weight—0.01 to 10 wt. %, preferably 0.05 to 7 wt. %, particularly preferably 0.1 to 5 wt. %, more preferably 0.25 to 2.5 wt. % and in particular 0.5 to 2.0 wt. % protein hydrolyzate(s), preferably keratin hydrolyzate(s).

For aesthetic reasons, "clear" products are often preferred by consumers. Preferred hair treatment agents according to the invention are therefore characterized in that they are transparent or translucent.

Within the framework of the present invention, transparent or translucent is understood to be a composition having an NTU value of less than 100. The NTU value (Nephelometric Turbidity Unit; NTU) is a unit used in water treatment for turbidity measurements in liquids. It is the unit of turbidity of a liquid measured with a calibrated nephelometer.

Furthermore, in a preferred embodiment of the invention, an agent according to the invention can also include UV filters (I). The UV filters to be used according to the invention are not subject to any general restrictions with regard to their structure and their physical properties. Rather, all UV filters that can be used in the cosmetics sector having an absorption maximum in the UVA (315-400 nm), in the UVB (280-315 nm) or in the UVC (<280 nm) range are suitable. UV filters with an absorption maximum in the UVB range, in particular in the range of about 280 to about 300 nm, are particularly preferred.

The UV filters used according to the invention can be selected e.g. from substituted benzophenones, p-aminobenzoic acid esters, diphenylacrylic acid esters, cinnamic acid esters, salicylic acid esters, benzimidazoles and o-aminobenzoic acid esters.

Examples of UV filters that can be used according to the invention are 4-aminobenzoic acid, N,N,N-trimethyl-4-(2-oxoborn-3-ylidenemethyl)aniline-methyl sulfate, 3,3,5-trimethylcyclohexyl salicylate (Homosalate), 2-hydroxy-4-methoxybenzophenone (Benzophenone-3; Uvinul®M 40, Uvasorb®MET, Neo Heliopan®BB, Eusolex®4360), 2-phenylbenzimidazole-5-sulfonic acid and potassium, sodium and triethanolamine salts thereof (phenylbenzimidazole sulfonic acid; Parsol® HS; Neo Heliopan®Hydro), 3,3'-(1,4-phenylenedimethylene)bis(7,7-dimethyl-2-oxobicyclo-[2.2.1]hept-1-ylmethanesulfonic acid) and salts thereof, 1-(4-tert.-butylphenyl)-3-(4-methoxyphenyl)-propane-1,3-dione (butyl methoxydibenzoylmethane; Parsol®1789, Eusolex® 9020), α-(2-oxoborn-3-ylidene)toluene-4-sulfonic acid and salts thereof, ethoxylated 4-aminobenzoic acid ethyl ester (PEG-25 PABA; Uvinul®P 25), 4-dimethylaminobenzoic acid 2-ethylhexyl ester (octyl dimethyl PABA; Uvasorb® DMO, Escalol® 507, Eusolex®6007), salicylic acid 2-ethylhexyl ester (octyl salicylate; Escalol®587, Neo Heliopan®OS, Uvinul®O18), 4-methoxycinnamic acid isopentyl ester (Isoamyl p-Methoxycinnamate; Neo Heliopan®E 1000), 4-methoxycinnamic acid 2-ethylhexyl ester (octyl methoxycinnamate; Parsol®MCX, Escalol®557, Neo Heliopan®AV), 2-hydroxy-4-methoxybenzophenone-5-sulfonic acid and sodium salt thereof (Benzophenone-4; Uvinul® MS 40; Uvasorb® S 5), 3-(4'-methylbenzylidene)-D,L-camphor (4-Methylbenzylidene Camphor; Parsol®5000, Eusolex®6300), 3-benzylidene camphor (3-Benzylidene Camphor), 4-isopropylbenzyl salicylate, 2,4,6-trianilino-(p-carbo-2'-ethylhexyl-1-oxy)-1,3,5-triazine, 3-imidazol-4-yl-acrylic acid and ethyl ester thereof, polymers of N-{(2 and 4)-[2-oxoborn-3-ylidenemethyl] benzyl}acrylamide, 2,4-dihydroxybenzophenone (Benzophenone-1; Uvasorb®20 H, Uvinul®400), 1,1'-diphenylacrylonitrile acid 2-ethylhexyl ester (Octocrylene; Eusolex® OCR, Neo Heliopan® Type 303, Uvinul®M 539 SG), o-aminobenzoic acid menthyl ester (Menthyl Anthranilate; Neo Heliopan®MA), 2,2',4,4'-tetrahydroxybenzophenone (Benzophenone-2; Uvinul®D-50), 2,2'-dihydroxy-4,4'-dimethoxybenzophenone (Benzophenone-6), 2,2'-dihydroxy-4,4'-dimethoxybenzophenone-5-sodium sulfonate and 2-cyano-3,3-diphenylacrylic acid 2'-ethylhexyl ester. Preferred are 4-aminobenzoic acid, N,N,N-trimethyl-4-(2-oxoborn-3-ylidenemethyl)aniline methyl sulfate, 3,3,5-trimethylcyclohexyl salicylate, 2-hydroxy-4-methoxybenzophenone, 2-phenylbenzimidazole-5-sulfonic acid and potassium, sodium and triethanolamine salts thereof, 3,3'41,4-phenylenedimethylene)bis(7,7-dimethyl-2-oxobicyclo-[2.2.1]hept-1-ylmethanesulfonic acid) and salts thereof, 1-(4-tert.-butylphenyl)-3-(4-methoxyphenyl)propane-1,3-dione, α-(2-oxoborn-3-ylidene)-toluene-4-sulfonic acid and salts thereof, ethoxylated 4-aminobenzoic acid ethyl ester, 4-dimethylaminobenzoic acid 2-ethylhexyl ester, salicylic acid 2-ethylhexyl ester, 4-methoxycinnamic acid isopentyl ester, 4-methoxycinnamic acid 2-ethylhexyl ester, 2-hydroxy-4-methoxybenzophenone-5-sulfonic acid and sodium salt thereof, 3-(4'-methylbenzylidene) D,L-camphor, 3-benzylidene camphor, 4-isopropylbenzyl salicylate, 2,4,6-trianilino-(p-carbo-2'-ethylhexyl-1'-oxy)-1,3,5-triazine, 3-imidazol-4-ylacrylic acid and ethyl ester thereof, polymers of N-{(2 and 4)-[2-oxoborn-3-ylidenemethyl] benzyl}acrylamide. Most particularly preferred according to the invention are 2-hydroxy-4-methoxybenzophenone, 2-phenylbenzimidazole-5-sulfonic acid and potassium, sodium and triethanolamine salts thereof, 1-(4-tert.-butylphenyl)-3-(4-methoxyphenye-propane-1,3-dione, 4-methoxycinnamic acid 2-ethylhexyl ester and 3-(4'-methylbenzylidene) D,L-camphor.

Those UV filters of which the molar extinction coefficient at the absorption maximum is above 15 000, in particular above 20 000, are preferred.

It has furthermore been found that in many cases, with structurally similar UV filters, the water-insoluble compound within the framework of the teaching according to the invention has the higher activity compared with those water-soluble compounds that differ from it by one or more additional ionic groups. Those UV filters that dissolve in water at 20° C. in a quantity of no more than 1 wt. %, in particular no more than 0.1 wt. %, are understood as water-insoluble within the framework of the invention. Furthermore, these compounds should be soluble in conventional cosmetic oil components at room temperature in a quantity of at least 0.1, in particular at least 1 wt. %). The use of water-insoluble UV filters can therefore be preferred according to the invention.

In another preferred embodiment, the agents according to the invention can include emulsifiers (F). The agents according to the invention include the emulsifiers preferably in quantities of 0.1-25 wt. %, in particular 0.5-15 wt. %, based on the overall agent.

The compositions according to the invention can preferably include at least one non-ionogenic emulsifier with an HLB value of 8 to 18. Non-ionogenic emulsifiers with an HLB value of 10-15 can be particularly preferred according to the invention.

It has been shown to be furthermore advantageous if, in addition to the polymer(s) from the group of the cationic and/or amphoteric polymers, other polymers (G) are included in the agents according to the invention. In a preferred embodiment, therefore, other polymers are added to the agents according to the invention, both anionic and nonionic polymers having proved effective.

The anionic polymers (G2) are anionic polymers having carboxylate and/or sulfonate groups. Examples of anionic monomers of which polymers of this type can consist are acrylic acid, methacrylic acid, crotonic acid, maleic anhydride and 2-acrylamido-2-methylpropanesulfonic acid. The acidic groups here can be entirely or partially present as a sodium, potassium, ammonium, mono- or triethanolammonium salt. Preferred monomers are 2-acrylamido-2-methylpropanesulfonic acid and acrylic acid.

Anionic polymers which include 2-acrylamido-2-methylpropanesulfonic acid as sole monomer or comonomer, wherein the sulfonic acid group can be present entirely or partially as a sodium, potassium, ammonium, mono- or triethanolammonium salt, have proved most particularly effective.

Particularly preferred is the homopolymer of 2-acrylamido-2-methylpropanesulfonic acid, which is commercially available for example with the name Rheothik 11-80.

Within this embodiment it can be preferred to use copolymers of at least one anionic monomer and at least one non-ionogenic monomer. With regard to the anionic monomers, reference is made to the substances listed above. Preferred non-ionogenic monomers are acrylamide, methacrylamide, acrylic acid ester, methacrylic acid ester, vinylpyrrolidone, vinyl ether and vinyl ester.

Preferred anionic copolymers are acrylic acid-acrylamide copolymers and, in particular, polyacrylamide copolymers with monomers including sulfonic acid groups. A particularly preferred anionic copolymer consists of 70 to 55 mole % acrylamide and 30 to 45 mole % 2-acrylamido-2-methylpropanesulfonic acid, wherein the sulfonic acid group is present entirely or partially as a sodium, potassium, ammonium, mono- or triethanolammonium salt. This copolymer can also be present in crosslinked form, in which case preferably polyolefinically unsaturated compounds such as tetraallyloxyethane, allyl sucrose, allyl pentaerythritol and methylene bisacrylamide are used as crosslinking agents. A polymer of this type is included in the commercial product Sepigel®305 from SEPPIC. The use of this compound, which in addition to the polymer component includes a hydrocarbon mixture ($C_{13}$-$C_{14}$ isoparaffin) and a non-ionogenic emulsifier (laureth-7), has proved particularly advantageous within the framework of the teaching according to the invention.

The sodium acryloyldimethyl taurate copolymers which are marketed with the name Simulgel®600 as a compound with isohexadecane and polysorbate-80 have also proved particularly effective according to the invention.

Likewise preferred anionic homopolymers are uncrosslinked and crosslinked polyacrylic acids. In this case, allyl ethers of pentaerythritol, of sucrose and of propylene can be preferred crosslinking agents. These compounds are commercially available for example with the trade mark Carbopol®.

Copolymers of maleic anhydride and methyl vinyl ether, in particular those with crosslinkages, are also color-retaining polymers. A maleic acid-methyl vinyl ether copolymer crosslinked with 1,9-decadiene is commercially available with the name Stabileze® QM.

In a further embodiment, the agents according to the invention can include non-ionogenic polymers (G4).

Suitable non-ionogenic polymers are e.g.:
a. Vinyl pyrrolidone/vinyl ester copolymers, as marketed e.g. with the trade mark Luviskol® (BASF). Luviskol® VA 64 and Luviskol® VA 73, both vinyl pyrrolidone/vinyl acetate copolymers, are likewise preferred non-ionic polymers.
b. Cellulose ethers, such as hydroxypropyl cellulose, hydroxyethyl cellulose and methyl hydroxypropyl cellulose, as marketed e.g. with the trade marks Culminal® and Benecel® (AQUALON) and Natrosol® grades (Hercules).
c. Starch and derivatives thereof, in particular starch ethers, e.g. Structure XL (National Starch), a multi-functional, salt-tolerant starch;
d. Shellac
e. Polyvinyl pyrrolidones, as marketed e.g. with the name Luviskol® (BASF).
f. Siloxanes. These siloxanes can be both water-soluble and water-insoluble. Both volatile and non-volatile siloxanes are suitable, with non-volatile siloxanes being understood as those compounds of which the boiling point under standard pressure is above 200° C. Preferred siloxanes are polydialkylsiloxanes, such as e.g. polydimethylsiloxane, polyalkylarylsiloxanes, such as e.g. polyphenylmethylsiloxane, ethoxylated polydialkylsiloxanes and polydialkylsiloxanes including amine and/or hydroxy groups.
g. Glycosidically substituted silicones.

It is also possible according to the invention for the preparations to include several, in particular two different polymers with the same charge and/or in each case an ionic and an amphoteric and/or nonionic polymer.

The other polymers (G) are included in the agents according to the invention preferably in quantities of 0.05 to 10 wt. %, based on the overall agent. Quantities of 0.1 to 5, in particular of 0.1 to 3 wt. %, are particularly preferred.

The present invention also provides a method for treating keratinic fibers, in which a treatment agent according to the invention is applied onto the keratinic fibers and after an exposure time of a few seconds to 45 minutes is rinsed out again.

With regard to preferred embodiments of the method according to the invention, the statements made relating to the agents according to the invention apply mutatis mutandis.

The present invention also provides the use of hair treatment agents according to the invention
to improve the wet and dry combability and/or
to improve the gloss and/or
to improve the moisture balance of keratinic fibers and/or
to protect the keratinic fibers from oxidative damage and/or
to prevent oiliness of keratinic fibers and/or
to increase the wash resistance of dyed keratinic fibers.

With regard to preferred embodiments of the uses according to the invention, the statements made relating to the agents according to the invention also apply mutatis mutandis.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A hair treatment agent including at least one 4-morpholinomethyl-substituted silicone, which in each case comprises at least one of the structural units of formulae (I), (II) and (III)

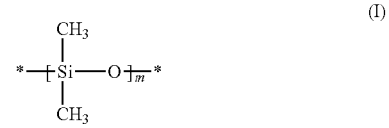

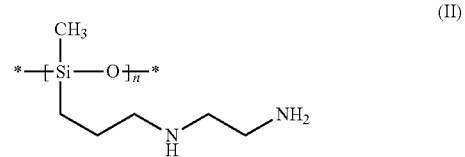

-continued

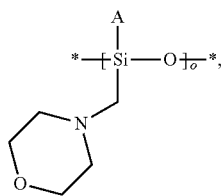
(III)

where
* denotes a bond to one of the structural units (I), (II) or (III) or an end group B (Si-bound) or D (O-bound),
B denotes a group —OH, —O—Si(CH₃)₃, —O—Si(CH₃)₂OH, —O—Si(CH₃)₂OCH₃,
D denotes a group —H; —Si(CH₃)₃, —Si(CH₃)₂OH, —Si(CH₃)₂OCH₃,
A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH,
n, m and o denote integers between 1 and 1000.

2. A hair treatment agent including at least one 4-morpholinomethyl-substituted silicone of formula (IV)

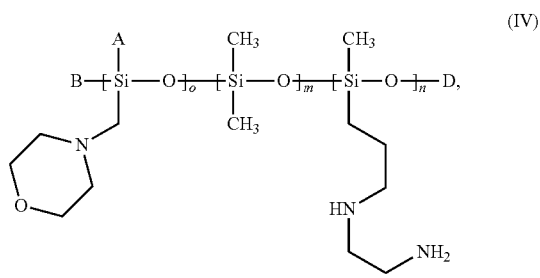
(IV)

in which
A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH,
B denotes a group —OH, —O—Si(CH₃)₃, —O—Si(CH₃)₂OH, —O—Si(CH₃)₂OCH₃,
D denotes a group —H; —Si(CH₃)₃, —Si(CH₃)₂OH, —Si(CH₃)₂OCH₃,
n, m and o denote integers between 1 and 1000, the siloxane units m, n and o being present in random distribution.

3. The hair treatment agent according to claim 1, wherein the agent includes at least one 4-morpholinomethyl-substituted silicone of formula (V)

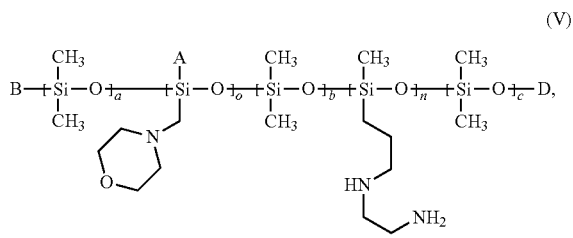
(V)

in which
A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH,
B denotes a group —OH, —O—Si(CH₃)₃, —O—Si(CH₃)₂OH, —O—Si(CH₃)₂OCH₃,
D denotes a group —H; —Si(CH₃)₃, —Si(CH₃)₂OH, —Si(CH₃)₂OCH₃,
a, b and c denote integers between 0 and 1000, with the proviso that a+b+c>0
n and o denote integers between 1 and 1000.

4. The hair treatment agent according to claim 1, wherein the agent includes at least one 4-morpholinomethyl-substituted silicone, which comprises structural units of formula (VI)

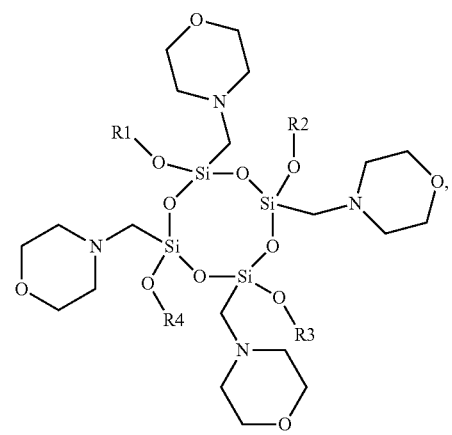
(VI)

in which
R1, R2, R3 and R4 independently of one another denote —H, —CH₃, a group D, a structural unit (I), (II) or (III) or an oligomeric or polymeric residue including structural units of formulae (I), (II) or (III) or
two of the residues R1, R2, R3 and R4 denote a structural unit —Si(R6)(R5)- with
R5=—CH₃ or a structural unit of formula (I) or (II) or (III) or an oligomeric or polymeric residue including structural units of formulae (I), (II) or (III)
R6=—OH, —CH₃ or a structural unit of formula (I) or (II) or (III) or an oligomeric or polymeric residue including structural units of formulae (I), (II) or (III).

5. The hair treatment agent according to claim 1, wherein the agent includes at least one 4-morpholinomethyl-substituted silicone, which comprises structural units of formula (VII)

(VII)

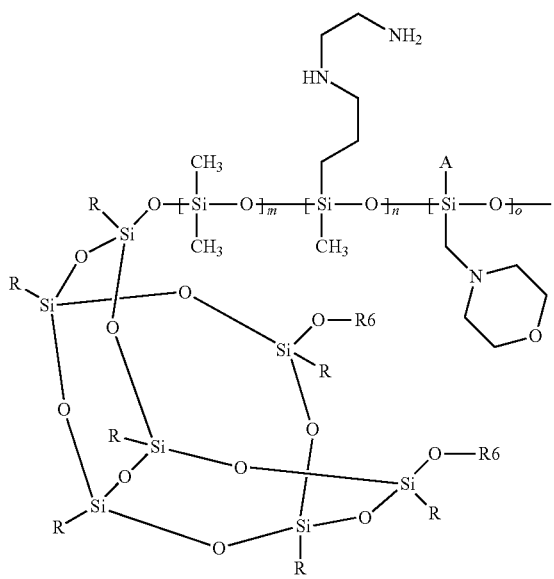

in which
A denotes a structural unit (I), (II) or (III) bound by an —O— or an oligomeric or polymeric residue including structural units of formulae (I), (II) or (III) bound by an —O— or half of a connecting O atom to a structural unit (III) or denotes —OH,
D denotes a group —H, —Si(CH$_3$)$_3$, —Si(CH$_3$)$_2$OH, —Si(CH$_3$)$_2$OCH$_3$,
R denotes a residue 4-morpholinomethyl,
R6 denotes —H or the grouping

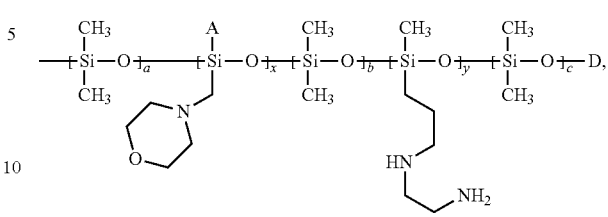

the siloxane units m, n and o and a, b, x and y respectively being present in random distribution.

6. The hair treatment agent according to claim 1, wherein the agent includes at least one 4-morpholinomethyl-substituted silicone, in which the following apply:
m>(n+o) and (a+b+c)>(n+o) respectively.

7. The hair treatment agent according to claim 1, wherein the agent includes—based on its weight—0.00001 to 10 wt. % 4-morpholinomethyl-substituted silicone(s).

8. The hair treatment agent according to claim 1, wherein the agent includes—based on its weight—0.00001 to 5 wt. % branched, ethoxylated tridecanol (INCI name: Trideceth-5) or α-iso-tridecyl-w-hydroxy polyglycol ether (INCI name: Trideceth-10) or mixtures thereof.

9. A method for treating keratinic fibers, comprising:
applying a hair treatment agent according to claim 1 onto the keratinic fibers, and
rinsing the agent out again after an exposure time of a few seconds to 45 minutes.

* * * * *